US 8,668,964 B2

(12) United States Patent
Kato et al.

(10) Patent No.: US 8,668,964 B2
(45) Date of Patent: Mar. 11, 2014

(54) DIOXOLANE COMPOUND, LIQUID CRYSTAL COMPOSITION, LIQUID CRYSTAL ELEMENT, AND LIQUID CRYSTAL DISPLAY DEVICE

(71) Applicant: Semiconductor Energy Laboratory Co., Ltd., Atsugi (JP)

(72) Inventors: Momoko Kato, Kanagawa (JP); Yuko Kawata, Kanagawa (JP); Tetsuji Ishitani, Kanagawa (JP); Yasuhiro Niikura, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 13/686,090

(22) Filed: Nov. 27, 2012

(65) Prior Publication Data

US 2013/0134353 A1    May 30, 2013

(30) Foreign Application Priority Data

Nov. 29, 2011 (JP) ................. 2011-260727

(51) Int. Cl.
*C09K 19/54* (2006.01)
*C09K 19/52* (2006.01)
*C07D 317/22* (2006.01)

(52) U.S. Cl.
USPC ............... 428/1.1; 252/299.01; 252/299.5; 549/453

(58) Field of Classification Search
CPC ...................................... C09K 19/588
USPC ............. 549/453; 252/299.01, 299.5; 428/1.1
See application file for complete search history.

(56) References Cited

U.S. PATENT DOCUMENTS

| | | | |
|---|---|---|---|
| 7,342,632 B2 | 3/2008 | Miyachi et al. | |
| 7,576,829 B2 | 8/2009 | Kikuchi et al. | |
| 7,648,647 B2 | 1/2010 | Kikuchi et al. | |
| 7,794,621 B2 | 9/2010 | Schott et al. | |
| 2009/0267025 A1 | 10/2009 | Schott et al. | |
| 2010/0195028 A1 | 8/2010 | Kubota et al. | |
| 2010/0258763 A1 | 10/2010 | Schott et al. | |
| 2011/0069245 A1 | 3/2011 | Haseba et al. | |
| 2012/0012785 A1 | 1/2012 | Schott et al. | |
| 2013/0009094 A1* | 1/2013 | Tamura et al. | 252/299.5 |

FOREIGN PATENT DOCUMENTS

| | | |
|---|---|---|
| DE | 10 2008 051 260 | 4/2010 |
| EP | 2 302 015 A1 | 3/2011 |
| JP | 2006-348226 | 12/2006 |
| JP | 2008-524347 | 7/2008 |
| JP | 2008-303381 | 12/2008 |
| JP | 2009-057459 | 3/2009 |
| WO | WO-2005-090520 A1 | 9/2005 |
| WO | WO-2006-063662 A1 | 6/2006 |
| WO | WO-2009-139330 A1 | 11/2009 |

OTHER PUBLICATIONS

CAPLUS 2010: 468733.*
Bauer, M. et al., "Evaluation of chiral dopants for LCD applications,", Journal of the SID, 2006, vol. 14, No. 9, pp. 805-812.
Goh.M et al., "Powerful helicity inducers: axially chiral binaphthyl derivatives ,", Liquid Crystals, Aug. 1, 2008, vol. 35, No. 8, pp. 953-965.
Kuball.H et al., "174. TADDOLs with Unprecedented Helical Twisting Power in Liquid Crystals,", Helvetica Chimica Acta, 1997, vol. 80, No. 8, pp. 2507-2514.

* cited by examiner

Primary Examiner — Shean C Wu
(74) Attorney, Agent, or Firm — Nixon Peabody LLP; Jeffrey L. Costellia

(57) ABSTRACT

A novel dioxolane compound represented by the general formula (G1) is provided. In the general formula (G1), $R^1$ and $R^2$ separately represent any of hydrogen, an alkylene group having 1 to 6 carbon atoms, an alkoxy group having 1 to 20 carbon atoms, an aryl group having 6 to 12 carbon atoms, and an alkylene group having 1 to 20 carbon atoms and a phenyl group as a substituent; $a^1$ and $a^2$ separately represent any of an alkylene group having 1 to 4 carbon atoms and a single bond; $Ar^1$ and $Ar^2$ separately represent an aryl group having 6 to 16 carbon atoms; and $R^3$ to $R^{38}$ separately represent any of hydrogen, an alkylene group having 1 to 4 carbon atoms, an alkoxy group having 1 to 4 carbon atoms, and an aryl group having 6 to 12 carbon atoms.

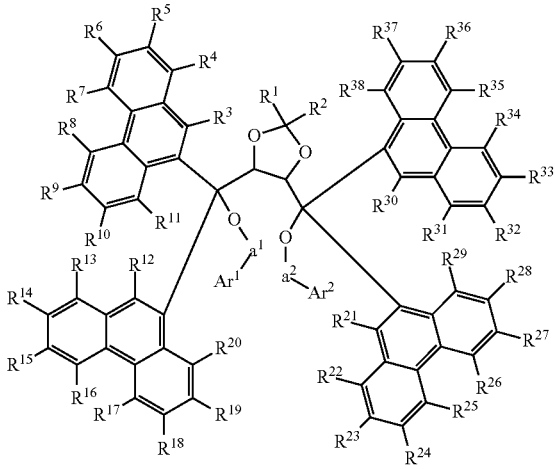

(G1)

18 Claims, 7 Drawing Sheets

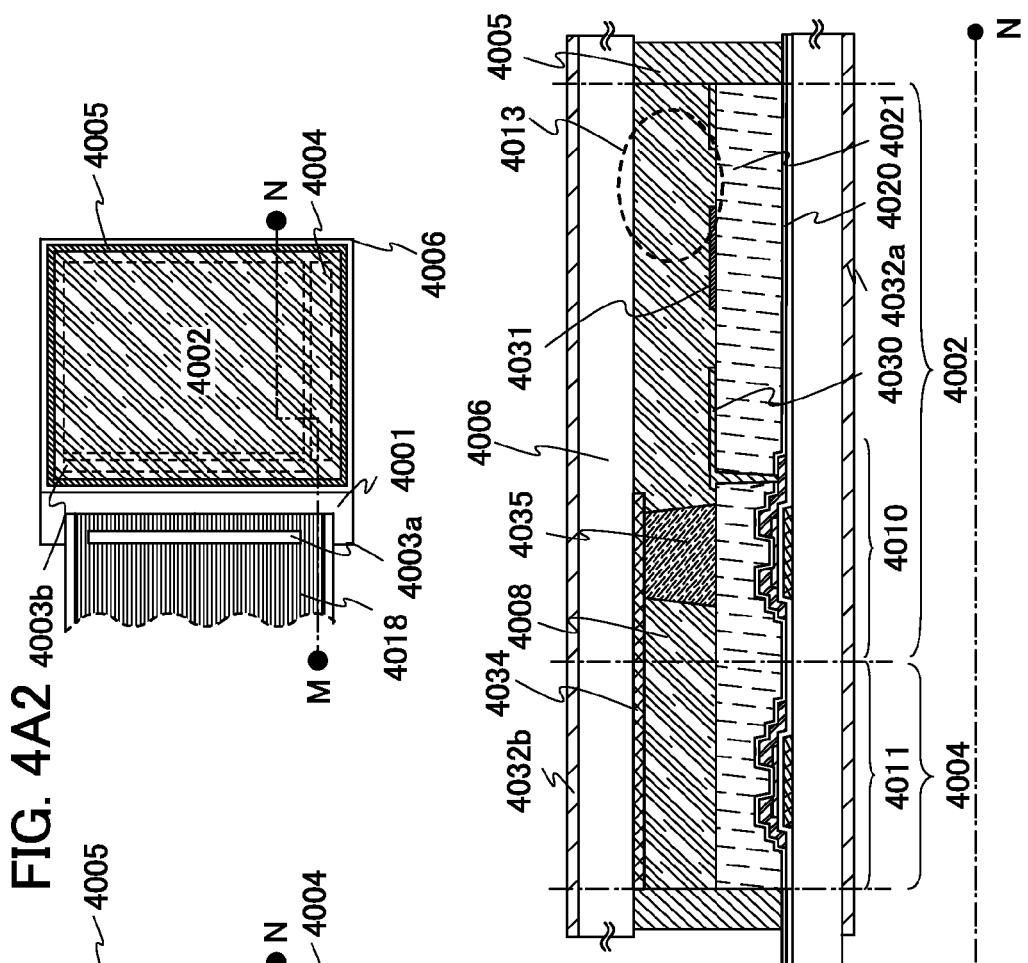

DIOXOLANE COMPOUND, LIQUID CRYSTAL COMPOSITION, LIQUID CRYSTAL ELEMENT, AND LIQUID CRYSTAL DISPLAY DEVICE

BACKGROUND OF THE INVENTION

1. Field of the Invention

One embodiment of the disclosed invention relates to a dioxolane compound, a liquid crystal composition that includes the dioxolane compound, a liquid crystal element and a liquid crystal display device that include the liquid crystal composition, and manufacturing methods thereof.

2. Description of the Related Art

In recent years, liquid crystal has been used for a variety of devices; in particular, a liquid crystal display device (liquid crystal display) having features of thinness and lightness has been used for displays in a wide range of fields.

For higher resolution of moving images and less so-called motion blur, shorter response time of liquid crystal has been required, and development thereof has been advanced (for example, see Patent Document 1).

As a display mode of liquid crystal capable of quick response, a display mode using a liquid crystal exhibiting a blue phase is given. The mode using a liquid crystal exhibiting a blue phase achieves quick response, does not require an alignment film, and provides a wide viewing angle, and thus has been developed more actively for practical use (for example, see Patent Document 2).

REFERENCE

Patent Document

[Patent Document 1] Japanese Published Patent Application No. 2008-303381
[Patent Document 2] PCT International Publication No. 2005-090520

SUMMARY OF THE INVENTION

An object is to provide a novel material for a liquid crystal composition or novel liquid crystal composition that can be used for a variety of liquid crystal devices.

One embodiment of the disclosed invention is a novel dioxolane compound represented by the following general formula (G1). The dioxolane compound can serve as a chiral agent in a liquid crystal composition.

(G1)

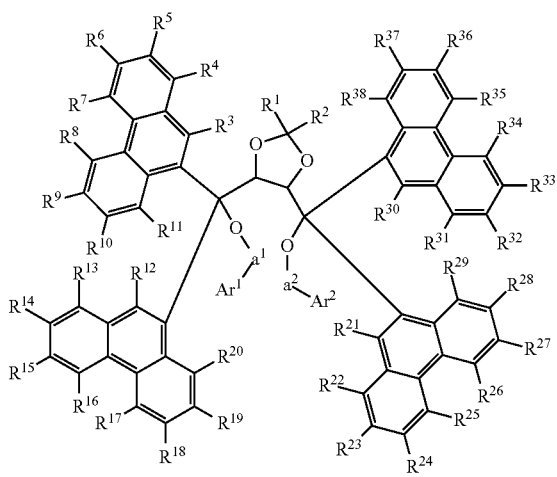

Note that in the general formula (G1), $R^1$ and $R^2$ separately represent any of hydrogen, an alkylene group having 1 to 6 carbon atoms, an alkoxy group having 1 to 20 carbon atoms, an aryl group having 6 to 12 carbon atoms, and an alkylene group having 1 to 20 carbon atoms and a phenyl group as a substituent; $R^1$ and $R^2$ may be bonded to each other to form a ring; $a^1$ and $a^2$ separately represent any of an alkylene group having 1 to 4 carbon atoms or a single bond; $Ar^1$ and $Ar^2$ separately represent an aryl group having 6 to 16 carbon atoms; and $R^3$ to $R^{38}$ separately represent any of hydrogen, an alkylene group having 1 to 4 carbon atoms, an alkoxy group having 1 to 4 carbon atoms, and an aryl group having 6 to 12 carbon atoms.

In the above liquid crystal composition, each of $a^1$ and $a^2$ is preferably a methylene group.

Another embodiment of the present invention is a dioxolane compound represented by the following general formula (G2).

(G2)

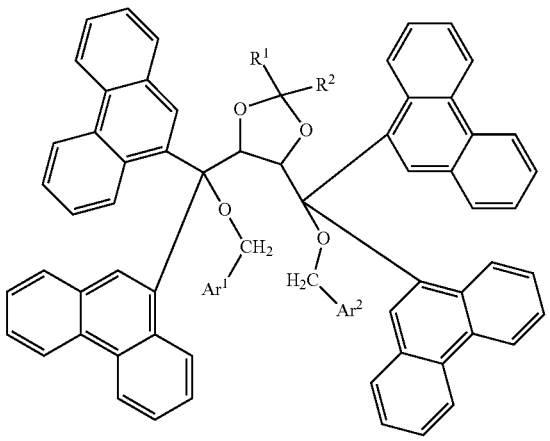

Note that in the general formula (G2), $R^1$ and $R^2$ separately represent any of hydrogen, an alkylene group having 1 to 6 carbon atoms, a methoxy group, and a phenyl group; $R^1$ and $R^2$ may be bonded to each other to form a cyclohexyl ring; and $Ar^1$ and $Ar^2$ separately represent an aryl group having 6 to 16 carbon atoms.

Another embodiment of the present invention is a dioxolane compound represented by the following general formula (G3).

(G3)

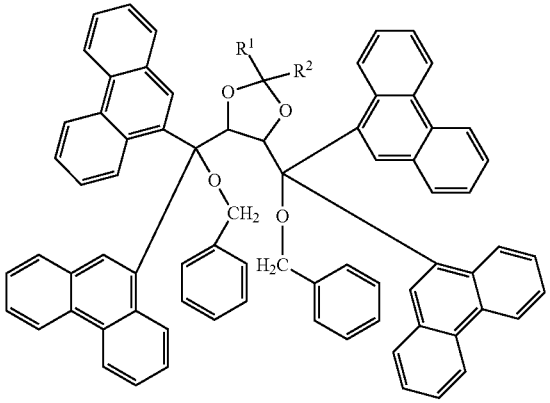

Note that in the general formula (G3), $R^1$ and $R^2$ separately represent any of hydrogen, an alkylene group having 1 to 6 carbon atoms, a methoxy group, and a phenyl group; and $R^1$ and $R^2$ may be bonded to each other to form a cyclohexyl ring.

Another embodiment of the present invention is a dioxolane compound represented by the following structural formula (101).

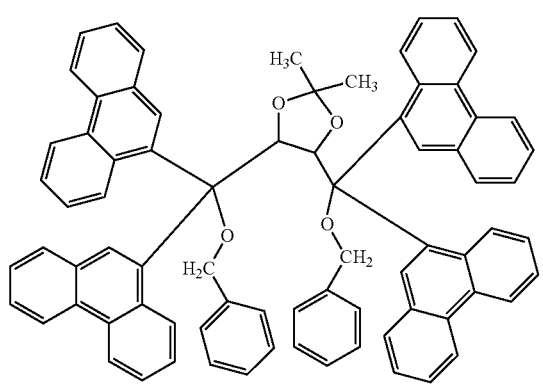

Another embodiment of the present invention is a liquid crystal composition including any of the above dioxolane compounds and a nematic liquid crystal, and exhibiting a blue phase. Note that a blue phase is exhibited in a liquid crystal composition having strong twisting power and has a double twist structure. The liquid crystal composition that can exhibit a blue phase shows a cholesteric phase, a cholesteric blue phase, an isotropic phase, or the like depending on conditions.

Indicators of the strength of twisting power include the helical pitch, the selective reflection wavelength, HTP (helical twisting power), and the diffraction wavelength. Among them, the helical pitch, the selective reflection wavelength, and HTP are used for evaluation of a cholesteric phase. On the other hand, the diffraction wavelength can be used for only evaluation of a blue phase, so that it is effective for evaluation of the twisting power of a blue phase. In the reflectance spectrum of a liquid crystal composition measured within the temperature range where the liquid crystal composition exhibits a blue phase, as the diffraction wavelength is on the shorter wavelength side, the liquid crystal composition has a smaller crystal lattice of a blue phase and stronger twisting power.

When the twisting power of the liquid crystal composition is strong, the transmittance of the liquid crystal composition in application of no voltage (at an applied voltage of 0 V) can be low, leading to a higher contrast of a liquid crystal display device including the liquid crystal composition.

The dioxolane compound represented by the general formula (G1) has a chiral center; therefore, when included in a liquid crystal composition, the dioxolane compound can serve as a chiral agent that induces twist of the liquid crystal composition to cause helical orientation, resulting in the exhibition of a blue phase.

Further, since the dioxolane compound represented by the general formula (G1) is a chiral agent with strong twisting power, the proportion thereof mixed in a liquid crystal composition can be lower than or equal to 15 wt %, preferably lower than or equal to 10 wt %, more preferably lower than or equal to 7 wt %. In general, when a large amount of chiral agent is added in order to improve the twisting power of the liquid crystal composition, driving voltage for driving a liquid crystal element including the liquid crystal composition might increase. However, in the liquid crystal composition according to one embodiment of the present invention, a smaller amount of chiral agent can be added, so that a reduction in the driving voltage of the liquid crystal element can be achieved. Thus, a reduction in power consumption of the liquid crystal display device including the liquid crystal composition can be achieved.

Further, one embodiment of the present invention also includes, in its category, a liquid crystal element, a liquid crystal display device, and an electronic appliance each including the above liquid crystal composition.

According to one embodiment of the present invention, a novel dioxolane compound represented by the above general formula (G1) can be provided. Further, a novel liquid crystal composition which includes the dioxolane compound represented by the above general formula (G1) as a chiral agent and a nematic liquid crystal and exhibits a blue phase can be provided.

BRIEF DESCRIPTION OF THE DRAWINGS

In the accompanying drawings:

FIGS. 4A1, 4A2, and 4B illustrate liquid crystal display modules;

DETAILED DESCRIPTION OF THE INVENTION

Figure 1A:
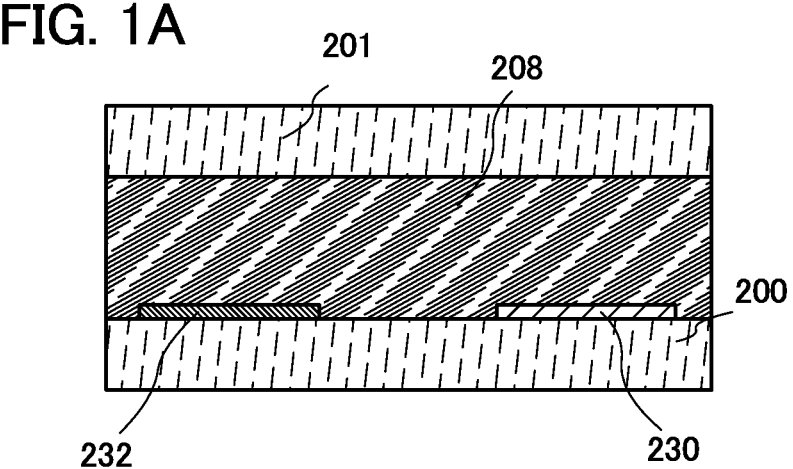
FIGS. 1A and 1B are conceptual diagrams each illustrating a liquid crystal compound and a liquid crystal composition.

Hereinafter, embodiments of the invention disclosed in this specification will be described in detail with reference to the accompanying drawings. Note that the invention disclosed in this specification is not limited to the following description, and it is easily understood by those skilled in the art that modes and details of the invention can be modified in various ways. Therefore, the invention disclosed in this specification is not construed as being limited to the description of the following embodiments or examples.

Embodiment 1

This embodiment shows a dioxolane compound according to one embodiment of the present invention.

One embodiment of the present invention is a dioxolane compound represented by the following general formula (G1).

(G1)

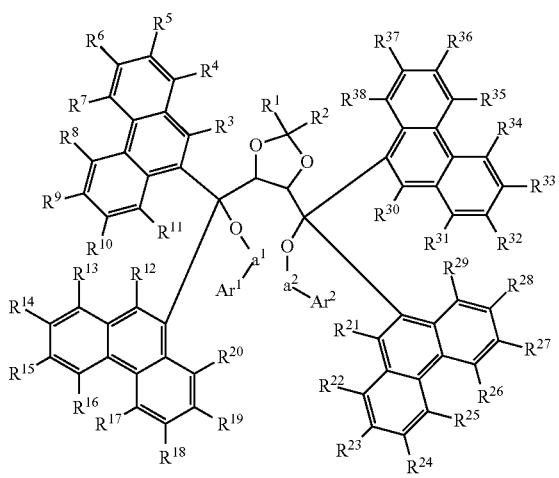

Note that in the general formula (G1), $R^1$ and $R^2$ separately represent any of hydrogen, an alkylene group having 1 to 6 carbon atoms, an alkoxy group having 1 to 20 carbon atoms, an aryl group having 6 to 12 carbon atoms, and an alkylene group having 1 to 20 carbon atoms and a phenyl group as a substituent; $R^1$ and $R^2$ may be bonded to each other to form a ring; $a^1$ and $a^2$ separately represent any of an alkylene group having 1 to 4 carbon atoms and a single bond; $Ar^1$ and $Ar^2$ separately represent an aryl group having 6 to 16 carbon atoms; and $R^3$ to $R^{38}$ separately represent any of hydrogen, an alkylene group having 1 to 4 carbon atoms, an alkoxy group having 1 to 4 carbon atoms, and an aryl group having 6 to 12 carbon atoms.

Note that the above compound preferably has an alkylene group having a few carbon atoms as each of $a^1$ and $a^2$ in the general formula (G1) for higher HTP of the dioxolane compound. Thus, each of $a^1$ and $a^2$ in the general formula (G1) is preferably a methylene group.

Another embodiment of the present invention is a dioxolane compound represented by the following general formula (G2).

(G2)

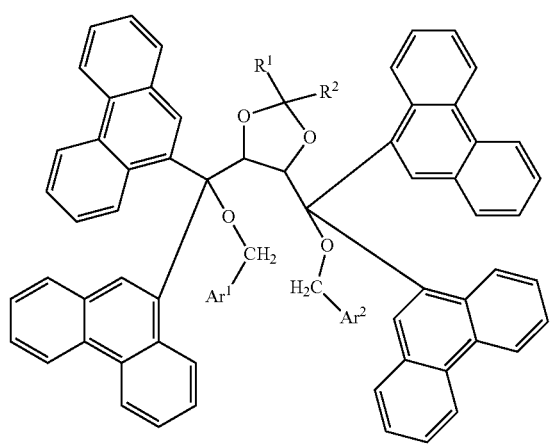

Note that in the general formula (G2), $R^1$ and $R^2$ separately represent any of hydrogen, an alkylene group having 1 to 6 carbon atoms, a methoxy group, and a phenyl group; $R^1$ and $R^2$ may be bonded to each other to form a cyclohexyl ring; and $Ar^1$ and $Ar^2$ separately represent an aryl group having 6 to 16 carbon atoms.

Another embodiment of the present invention is a dioxolane compound represented by the following general formula (G3).

(G3)

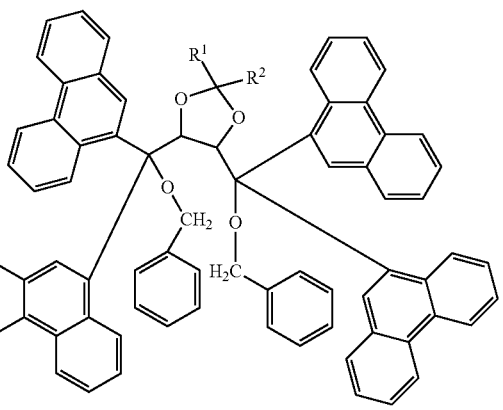

Note that in the general formula (G3), $R^1$ and $R^2$ separately represent any of hydrogen, an alkylene group having 1 to 6 carbon atoms, a methoxy group, and a phenyl group; and $R^1$ and $R^2$ may be bonded to each other to form a cyclohexyl ring.

Specific examples of the dioxolane compound represented by the above general formula (G1) include dioxolane compounds represented by structural formulas (100) to (111). However, the present invention is not limited to these examples.

(100)

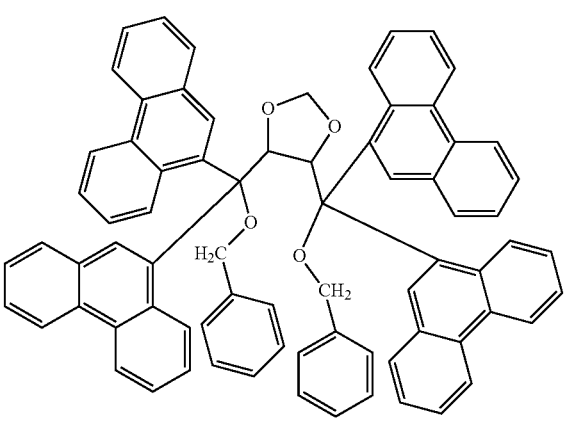

(101)
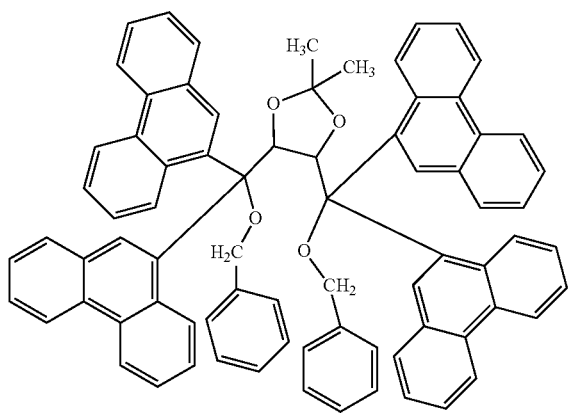
(102)
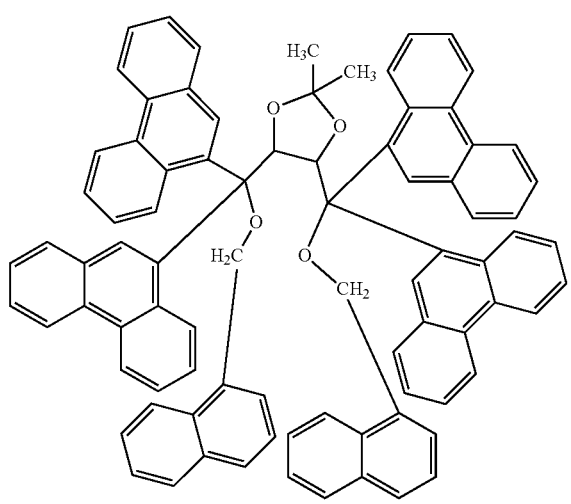
(103)
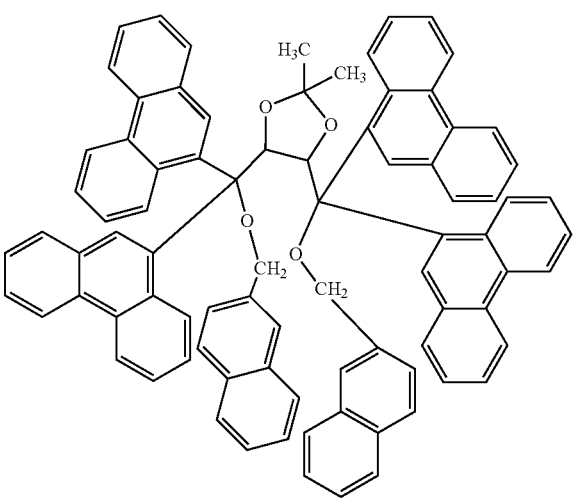
(104)
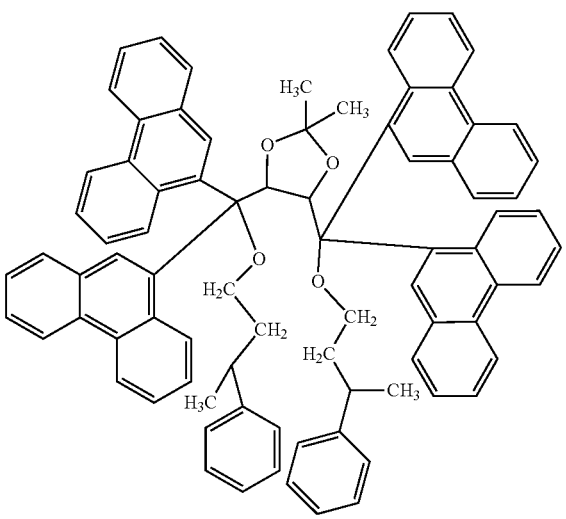
(105)
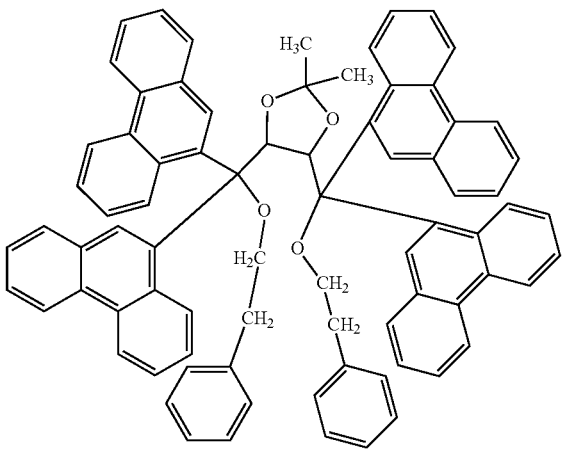
(106)
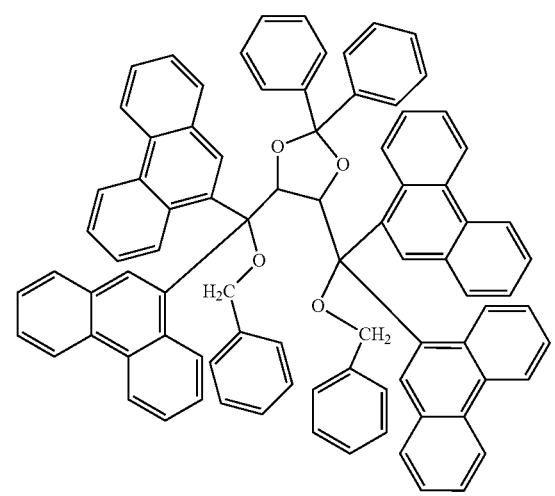

(107)

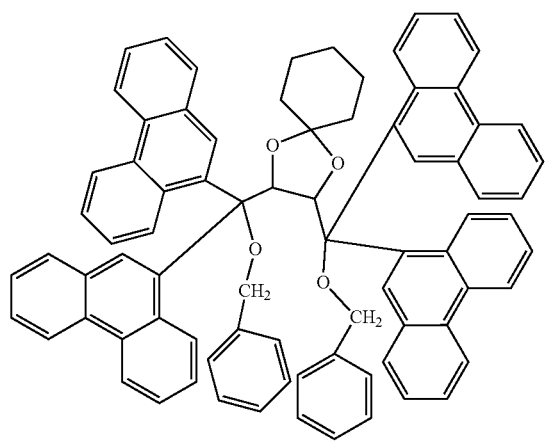

(108)

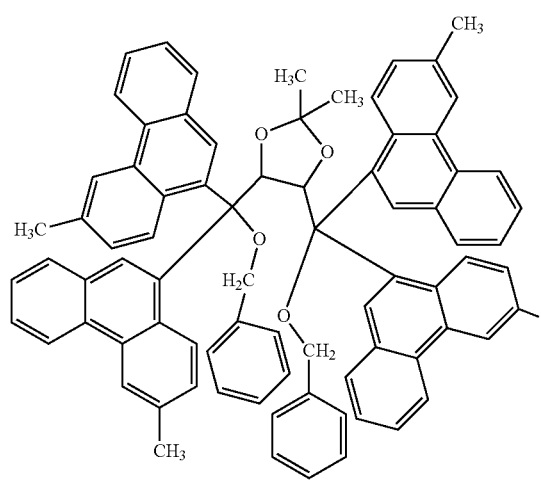

(109)

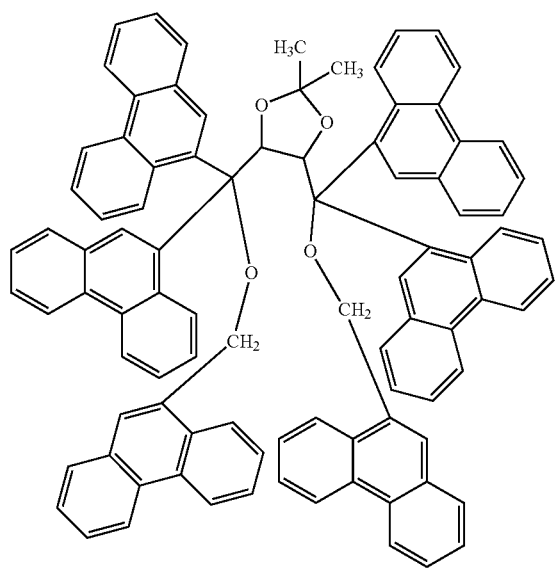

(110)

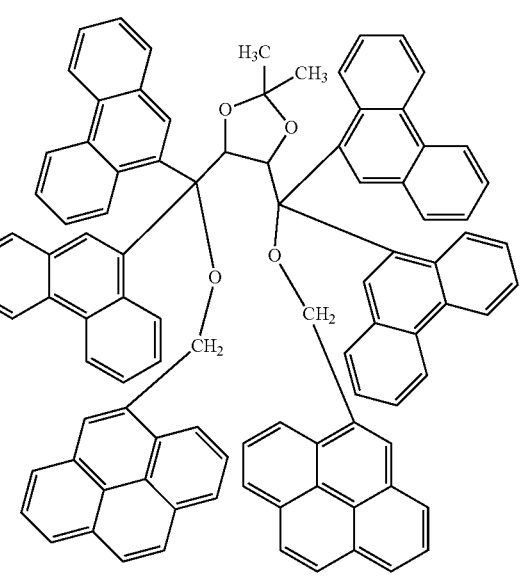

(111)

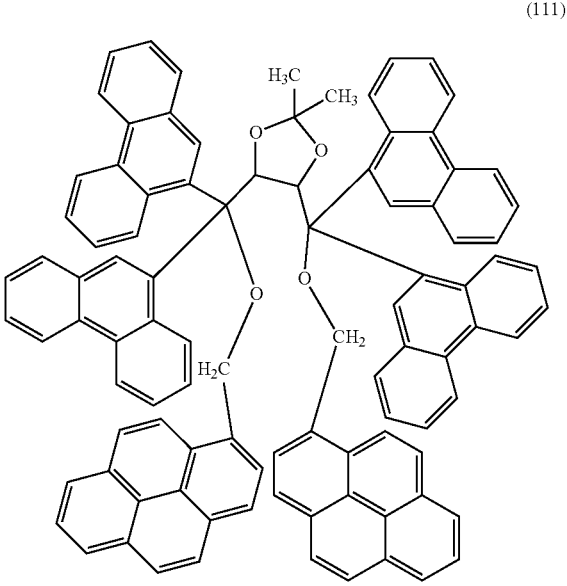

A variety of reactions can be applied to a synthesis method of the dioxolane compound represented by the general formula (G1) according to one embodiment of the present invention. For example, through synthesis reactions shown in the following synthesis scheme (K-1) or (K-2), the dioxolane compound represented by the general formula (G1) can be synthesized. Note that the synthesis method of the dioxolane compound represented by the general formula (G1) is not limited to the following synthesis method.

The following shows a synthesis method in the case where α, β, γ, and σ each representing a phenanthrene skeleton have the following relation α=β=γ=σ in the dioxolane compound represented by the general formula (G1).

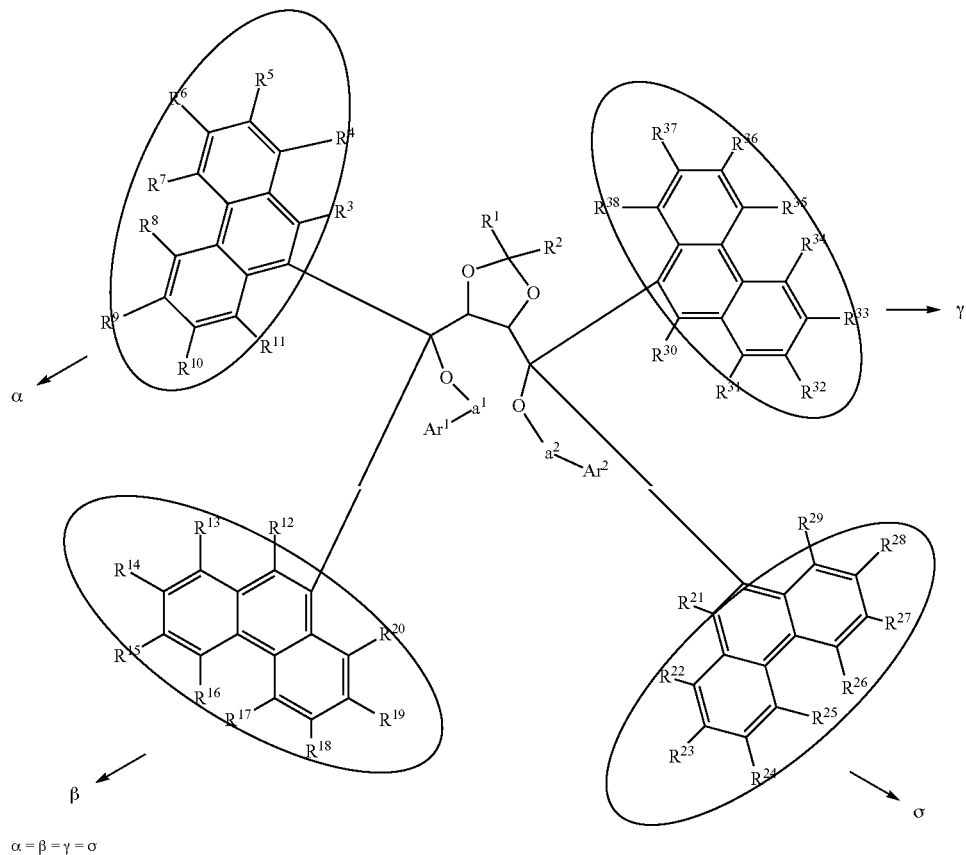
(G1)
α = β = γ = σ
In the case where the dioxolane compound represented by the general formula (G1) has the relation α=β=γ=σ, the general formula (G1) is represented by the following general formula (G1-1).
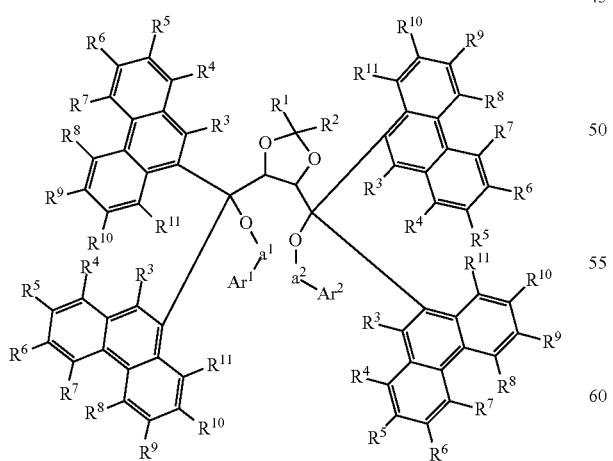
(G1-1)
The following shows a synthesis method of the dioxolane compound represented by the general formula (G1-1).

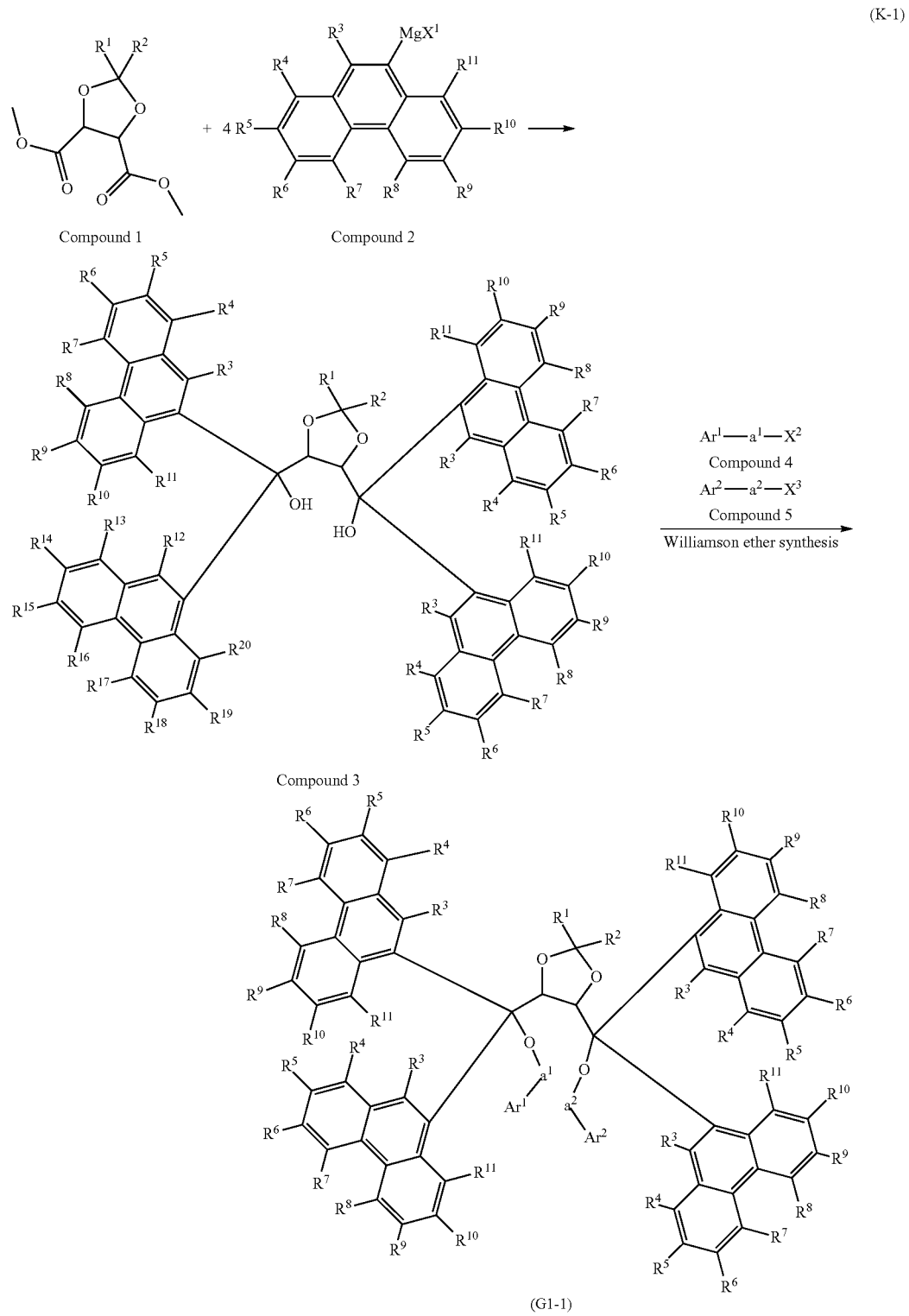

By making a compound having a 1,3-dioxolane-4,5-dicarboxylic acid skeleton (Compound 1) react with four equivalents of a Grignard reagent (Compound 2) which is a compound having a phenanthrene skeleton, a compound having a 1,3-dioxolane-4,5-diol skeleton (Compound 3) can be obtained. By substituting a hydroxyl group of Compound 3 with an alkoxy group through the Williamson ether synthesis reaction or the like using organic halides (Compound 4 and Compound 5, which may be the same compound), the target dioxolane compound (general formula (G1-1)) can be obtained (reaction formula (K-1)).

In the reaction formula (K-1), $R^1$ and $R^2$ separately represent any of hydrogen, an alkylene group having 1 to 6 carbon atoms, an alkoxy group having 1 to 6 carbon atoms, and an aryl group having 6 to 12 carbon atoms; and $R^1$ and $R^2$ may be bonded to each other to form a ring. Further, $a^1$ and $a^2$ separately represent any of an alkylene group having 1 to 4 carbon atoms and a single bond; $Ar^1$ and $Ar^2$ separately represent an aryl group having 6 to 16 carbon atoms; $R^3$ to $R^{11}$ separately represent any of hydrogen, an alkylene group having 1 to 4 carbon atoms, an alkoxy group having 1 to 4 carbon atoms, and an aryl group having 6 to 12 carbon atoms; and $X^1$, $X^2$, and $X^3$ separately represent any of iodine, bromine, and chlorine.

Note that in the reaction formula (K-1), a similar reaction can occur when instead of the Grignard reagent, a reagent having nucleophilicity such as a lithium compound is used as the compound having a phenanthrene skeleton, whereby the dioxolane compound represented by the general formula (G1-1) can be synthesized.

Alternatively, the dioxolane compound represented by the general formula (G1) can be synthesized by making the above Compound 1 react with the compound having a phenanthrene skeleton in four steps (reaction formula (K-2A) and reaction formula (K-2B)).

(K-2A)

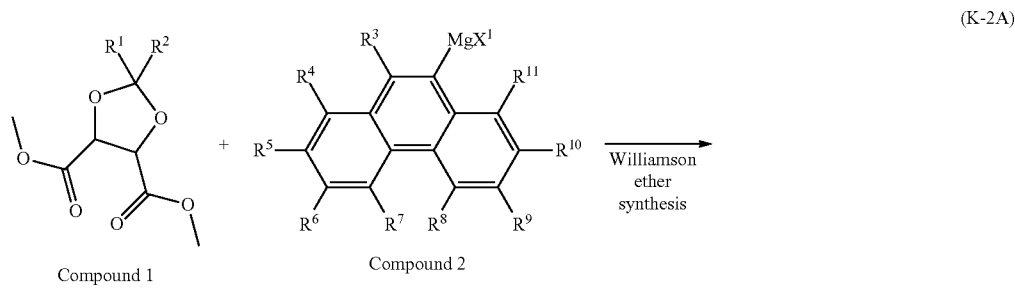

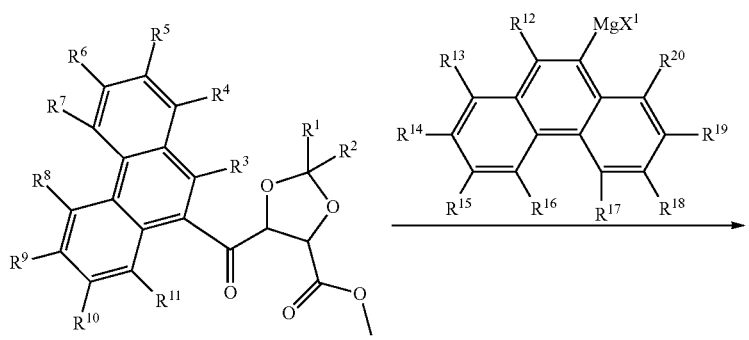

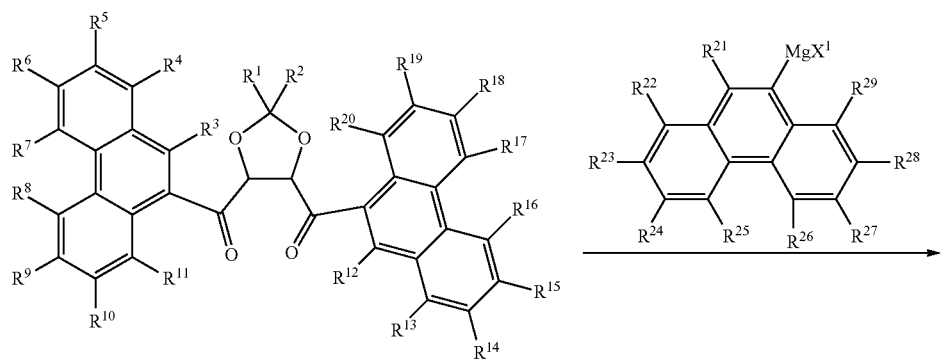

-continued
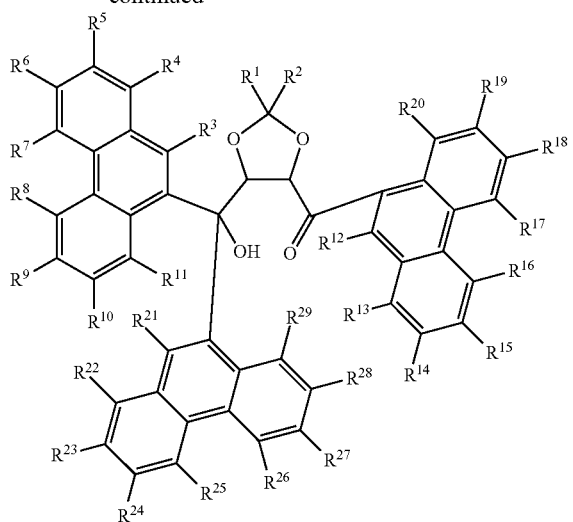
(K-2B)
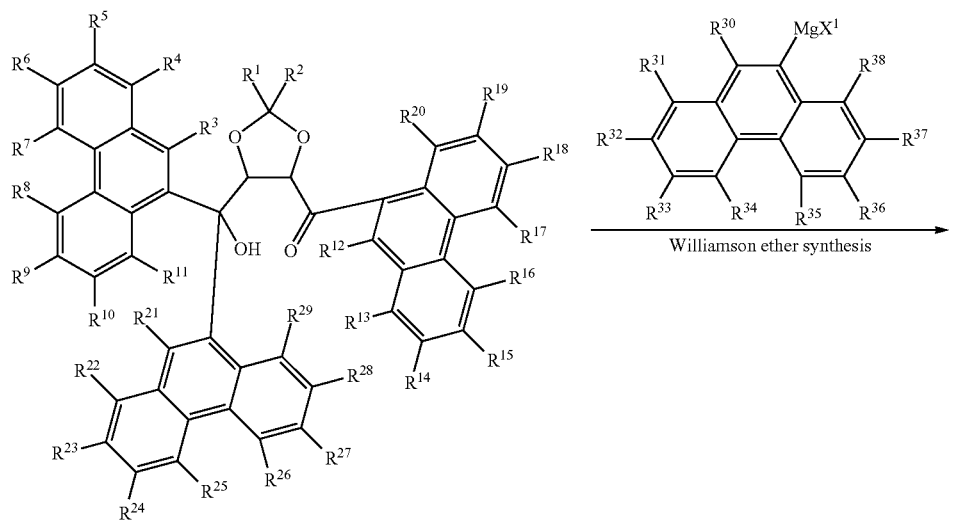
Williamson ether synthesis
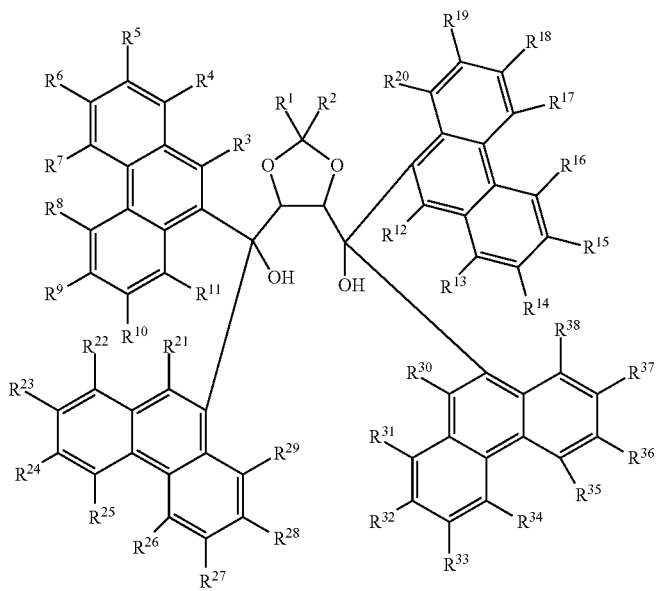
Ar¹—a¹—X²
Compound 4
Ar²—a²—X³
Compound 5
Williamson ether synthesis -continued

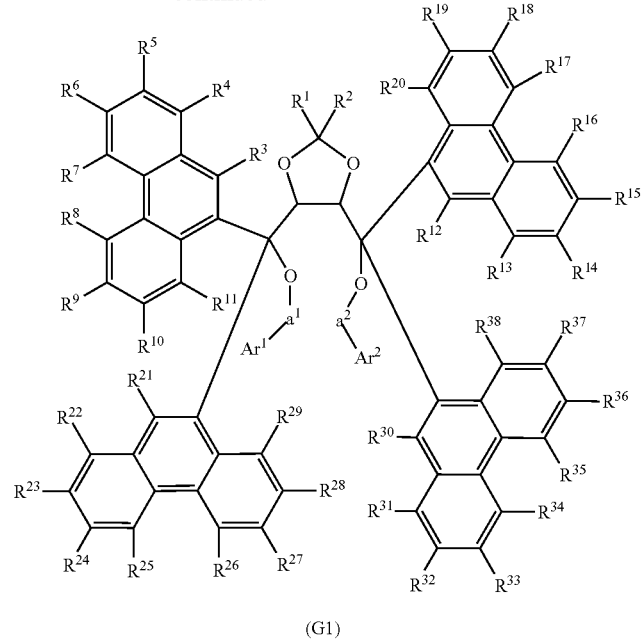

(G1)

In the above manner, the dioxolane compound represented by the general formula (G1) according to one embodiment of the present invention can be synthesized.

The dioxolane compound represented by the general formula (G1) has a chiral center; therefore, when included in a liquid crystal composition, the dioxolane compound can serve as a chiral agent that induces twist of the liquid crystal composition to cause helical orientation.

The liquid crystal composition including the dioxolane compound represented by the general formula (G1) as a chiral agent can be used for a liquid crystal display device in a lateral electric field mode such as a blue phase mode, a liquid crystal display device in a vertical electric field mode such as a TN mode, and the like.

The structures, methods, and the like described in this embodiment can be combined as appropriate with any of the other structures, methods, and the like described in the other embodiments.

Embodiment 2

In this embodiment, a liquid crystal composition including a dioxolane compound according to one embodiment of the present invention described in Embodiment 1, and a liquid crystal element or liquid crystal display device including the liquid crystal composition will be described with reference to FIGS. 1A and 1B.

The liquid crystal composition according to this embodiment includes at least the dioxolane compound described in Embodiment 1 and a nematic liquid crystal.

As described above, the dioxolane compound represented by the general formula (G1) can serve as a chiral agent. For example, the dioxolane compound represented by the general formula (G1) can be used as a chiral agent of a liquid crystal composition exhibiting a blue phase. Further, since the dioxolane compound represented by the general formula (G1) is a chiral agent with strong twisting power, the proportion thereof mixed in a liquid crystal composition can be lower than or equal to 15 wt %, preferably lower than or equal to 10 wt %, more preferably lower than or equal to 7 wt %.

There is no particular limitation on the nematic liquid crystal included in the liquid crystal composition according to one embodiment of the present invention, and examples thereof include a biphenyl-based compound, a terphenyl-based compound, a phenylcyclohexyl-based compound, a biphenylcyclohexyl-based compound, a phenylbicyclohexyl-based compound, a benzoic acid phenyl-based compound, a cyclohexyl benzoic acid phenyl-based compound, a phenyl benzoic acid phenyl-based compound, a bicyclohexyl carboxylic acid phenyl-based compound, an azomethine-based compound, an azo-based compound, an azoxy-based compound, a stilbene-based compound, a bicyclohexyl-based compound, a phenylpyrimidine-based compound, a biphenylpyrimidine-based compound, a pyrimidine-based compound, and a biphenyl ethyne-based compound.

Further, a blue phase is optically isotropic and thus has no viewing angle dependence. Consequently, an alignment film is not necessarily formed; thus, image quality of a display device can be improved and manufacturing cost can be reduced.

In a liquid crystal display device, it is preferable that a polymerizable monomer be added to a liquid crystal composition and polymer stabilization treatment be performed in order to broaden the temperature range within which a blue phase is exhibited. As the polymerizable monomer, for example, a thermopolymerizable (thermosetting) monomer which can be polymerized by heat, a photopolymerizable (photocurable) monomer which can be polymerized by light, or a polymerizable monomer which can be polymerized by heat and light can be used. Further, a polymerization initiator may be added to the liquid crystal composition.

The polymerizable monomer may be a monofunctional monomer such as acrylate or methacrylate; a polyfunctional monomer such as diacrylate, triacrylate, dimethacrylate, or trimethacrylate; or a mixture thereof. Further, the polymerizable monomer may have liquid crystallinity, non-liquid crystallinity, or a mixture of them.

As the polymerization initiator, a radical polymerization initiator which generates radicals by light irradiation, an acid generator which generates an acid by light irradiation, or a base generator which generates a base by light irradiation may be used.

For example, polymer stabilization treatment can be performed in such a manner that a photopolymerizable monomer and a photopolymerization initiator are added to the liquid crystal composition and the liquid crystal composition is irradiated with light having a wavelength at which the photopolymerizable monomer and the photopolymerization initiator react with each other. As the photopolymerizable monomer, typically, a UV polymerizable monomer can be used. When a UV polymerizable monomer is used as a photopolymerizable monomer, the liquid crystal composition may be irradiated with ultraviolet light.

This polymer stabilization treatment may be performed on a liquid crystal composition exhibiting an isotropic phase or a liquid crystal composition exhibiting a blue phase under the control of the temperature. A temperature at which the phase changes from a blue phase to an isotropic phase when the temperature rises, or a temperature at which the phase changes from an isotropic phase to a blue phase when the temperature falls is referred to as the phase transition temperature between a blue phase and an isotropic phase. For example, the polymer stabilization treatment can be performed in the following manner: after a liquid crystal composition to which a photopolymerizable monomer is added is heated to exhibit an isotropic phase, the temperature of the liquid crystal composition is gradually lowered so that the phase changes to a blue phase, and then, light irradiation is performed while the temperature at which a blue phase is exhibited is kept.

Figure 1B:
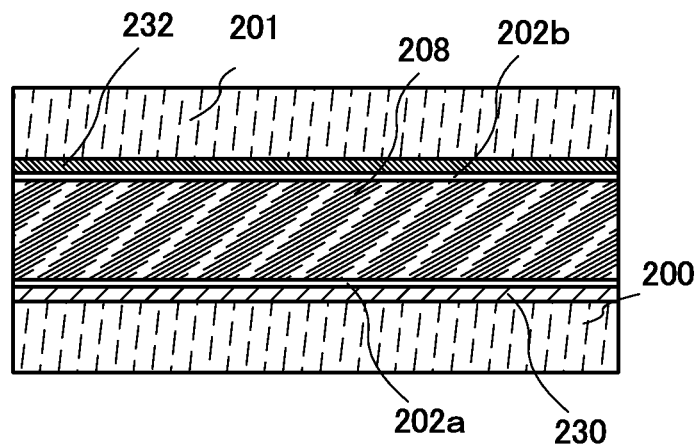

FIGS. 1A and 1B illustrate examples of a liquid crystal element and a liquid crystal display device according to embodiments of the present invention.

Note that in this specification and the like, a liquid crystal element is an element which controls transmission or non-transmission of light by an optical modulation action of liquid crystal and includes at least a pair of electrode layers and a liquid crystal composition interposed therebetween. A liquid crystal element in this embodiment includes at least, between a pair of electrode layers (a pixel electrode layer 230 and a common electrode layer 232 having different potentials), a liquid crystal composition 208 which includes the dioxolane compound represented by the general formula (G1) in Embodiment 1 and a nematic liquid crystal and which can exhibit a blue phase.

FIGS. 1A and 1B each illustrate a liquid crystal display device in which the liquid crystal composition 208 which includes the dioxolane compound represented by the general formula (G1) and a nematic liquid crystal and which exhibits a blue phase is provided between a first substrate 200 and a second substrate 201. A difference between the liquid crystal element and the liquid crystal display device in FIG. 1A and those in FIG. 1B is positions of the pixel electrode layer 230 and the common electrode layer 232 with respect to the liquid crystal composition 208.

In the liquid crystal element and the liquid crystal display device illustrated in FIG. 1A, the pixel electrode layer 230 and the common electrode layer 232 are provided between the first substrate 200 and the liquid crystal composition 208 so as to be adjacent to each other. With the structure in FIG. 1A, a method in which the gray scale is controlled by generating an electric field substantially parallel (i.e., in a lateral direction) to a substrate to move liquid crystal molecules in a plane parallel to the substrate can be used.

The structure in FIG. 1A can be favorably used for the case where the liquid crystal composition including the dioxolane compound represented by the general formula (G1) and a nematic liquid crystal and exhibiting a blue phase, which is a liquid crystal composition according to one embodiment of the present invention, is used as the liquid crystal composition 208. The liquid crystal composition provided as the liquid crystal composition 208 may contain an organic resin.

With an electric field formed between the pixel electrode layer 230 and the common electrode layer 232, a liquid crystal is controlled. An electric field in a lateral direction is formed for the liquid crystal, so that liquid crystal molecules can be controlled using the electric field. The liquid crystal composition exhibiting a blue phase is capable of quick response. Thus, a high-performance liquid crystal element and a high-performance liquid crystal display device can be provided. That is, the liquid crystal molecules aligned to exhibit a blue phase can be controlled in the direction parallel to the substrate, whereby a wide viewing angle can be obtained.

For example, such a liquid crystal composition exhibiting a blue phase is capable of quick response, and this can be favorably used for a successive additive color mixing method (a field sequential method) or a three-dimensional display method. In the successive additive color mixing method, light-emitting diodes (LEDs) of RGB or the like are arranged in a backlight unit and color display is performed by time division, and in the three-dimensional display method, a shutter glasses system is used in which images for a right eye and images for a left eye are alternately viewed by time division.

In the liquid crystal element and the liquid crystal display device illustrated in FIG. 1B, the pixel electrode layer 230 and the common electrode layer 232 are provided on the first substrate 200 side and the second substrate 201 side, respectively, with the liquid crystal composition 208 interposed therebetween. With the structure in FIG. 1B, a method in which the gray scale is controlled by generating an electric field substantially perpendicular to a substrate to move liquid crystal molecules in a plane perpendicular to the substrate can be used. An alignment film 202a and an alignment film 202b may be provided between the liquid crystal composition 208 and the pixel electrode layer 230 and between the liquid crystal composition 208 and the common electrode layer 232, respectively. A liquid crystal composition which includes the dioxolane compound represented by the general formula (G1) according to one embodiment of the present invention and a nematic liquid crystal can be used for liquid crystal elements with a variety of structures and liquid crystal display devices in a variety of display modes.

The pixel electrode layer 230 and the common electrode layer 232, which are adjacent to each other with the liquid crystal composition 208 interposed therebetween, have a distance at which liquid crystal in the liquid crystal composition 208 between the pixel electrode layer 230 and the common electrode layer 232 responds to a predetermined voltage which is applied to the pixel electrode layer 230 and the common electrode layer 232. The voltage applied is controlled depending on the distance as appropriate.

The maximum thickness (film thickness) of the liquid crystal composition 208 is preferably greater than or equal to 1 μm and less than or equal to 20 μm.

The liquid crystal composition 208 can be formed by a dispenser method (a dropping method), or an injection method by which liquid crystal is injected using capillary action or the like after the first substrate 200 and the second substrate 201 are attached to each other.

Although not illustrated in FIGS. 1A and 1B, an optical film such as a polarizing plate, a retardation plate, or an anti-reflection film, or the like is provided as appropriate. For example, circular polarization by the polarizing plate and the retardation plate may be used. In addition, a backlight or the like can be used as a light source.

In this specification, a substrate provided with a semiconductor element (e.g., a transistor) or a pixel electrode layer is referred to as an element substrate (a first substrate), and a substrate which faces the element substrate with a liquid crystal composition interposed therebetween is referred to as a counter substrate (a second substrate).

As a liquid crystal display device according to one embodiment of the present invention, a transmissive liquid crystal display device in which display is performed by transmission of light from a light source, a reflective liquid crystal display device in which display is performed by reflection of incident light, or a transflective liquid crystal display device in which a transmissive type and a reflective type are combined can be provided.

In the case of the transmissive liquid crystal display device, a pixel electrode layer, a common electrode layer, a first substrate, a second substrate, and other components such as an insulating film and a conductive film, which are provided in a pixel region through which light is transmitted, have a property of transmitting light in the visible wavelength range. In the liquid crystal display device having the structure illustrated in FIG. 1A, it is preferable that the pixel electrode layer and the common electrode layer have a light-transmitting property; however, if an opening pattern is provided, a non-light-transmitting material such as a metal film may be used depending on the shape.

On the other hand, in the case of the reflective liquid crystal display device, a reflective component which reflects light transmitted through the liquid crystal composition (e.g., a reflective film or substrate) may be provided on the side opposite to the viewing side of the liquid crystal composition. Therefore, a substrate, an insulating film, and a conductive film which are provided between the viewing side and the reflective component and through which light is transmitted have a light-transmitting property with respect to light in the visible wavelength range. Note that in this specification, a light-transmitting property refers to a property of transmitting at least light in the visible wavelength range. In the liquid crystal display device having the structure illustrated in FIG. 1B, the pixel electrode layer or the common electrode layer on the side opposite to the viewing side may have a light-reflecting property so that it can be used as a reflective component.

The pixel electrode layer 230 and the common electrode layer 232 may be formed with the use of one or more of the following: indium tin oxide (ITO), a conductive material in which zinc oxide (ZnO) is mixed into indium oxide, a conductive material in which silicon oxide ($SiO_2$) is mixed into indium oxide, organoindium, organotin, indium oxide containing tungsten oxide, indium zinc oxide containing tungsten oxide, indium oxide containing titanium oxide, and indium tin oxide containing titanium oxide; graphene; metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

As the first substrate 200 and the second substrate 201, a glass substrate of barium borosilicate glass, aluminoborosilicate glass, or the like, a quartz substrate, a plastic substrate, or the like can be used. Note that in the case of the reflective liquid crystal display device, a metal substrate such as an aluminum substrate or a stainless steel substrate may be used as a substrate on the side opposite to the viewing side.

With the use of the dioxolane compound represented by the general formula (G1) as a chiral agent in a liquid crystal composition, a smaller amount of chiral agent can be added to the liquid crystal composition. Therefore, by using the liquid crystal composition for a liquid crystal element or a liquid crystal display device, a liquid crystal element or liquid crystal display device that can be driven at a low driving voltage can be provided, and a reduction in power consumption of the liquid crystal display device can be achieved.

Further, the liquid crystal composition according to one embodiment of the present invention can exhibit a blue phase and respond quickly. Therefore, by using the liquid crystal composition for a liquid crystal element or a liquid crystal display device, a high-performance liquid crystal element or liquid crystal display device can be provided.

The structures, methods, and the like described in this embodiment can be combined as appropriate with any of the other structures, methods, and the like described in the other embodiments.

Embodiment 3

As a liquid crystal display device according to one embodiment of the present invention, a passive matrix liquid crystal display device and an active matrix liquid crystal display device can be provided. In this embodiment, an example of an active matrix liquid crystal display device according to one embodiment of the present invention will be described with reference to FIGS. 2A and 2B and FIGS. 3A to 3D.

Figure 2A:
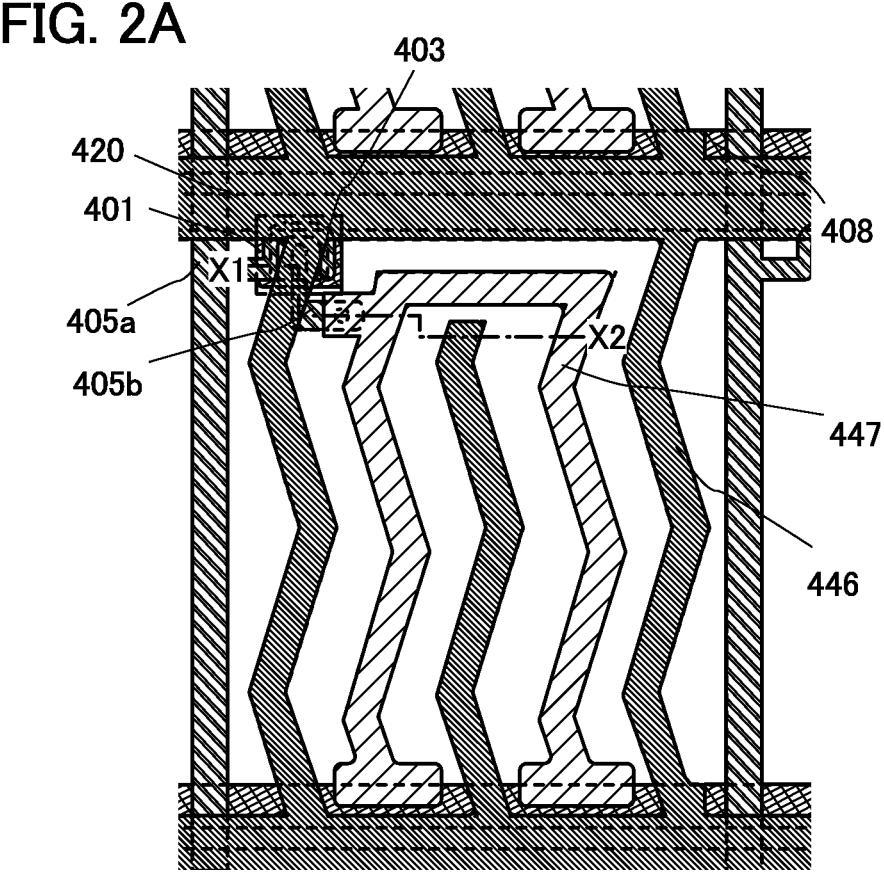
FIGS. 2A and 2B illustrate one mode of a liquid crystal display device.
Figure 2B:
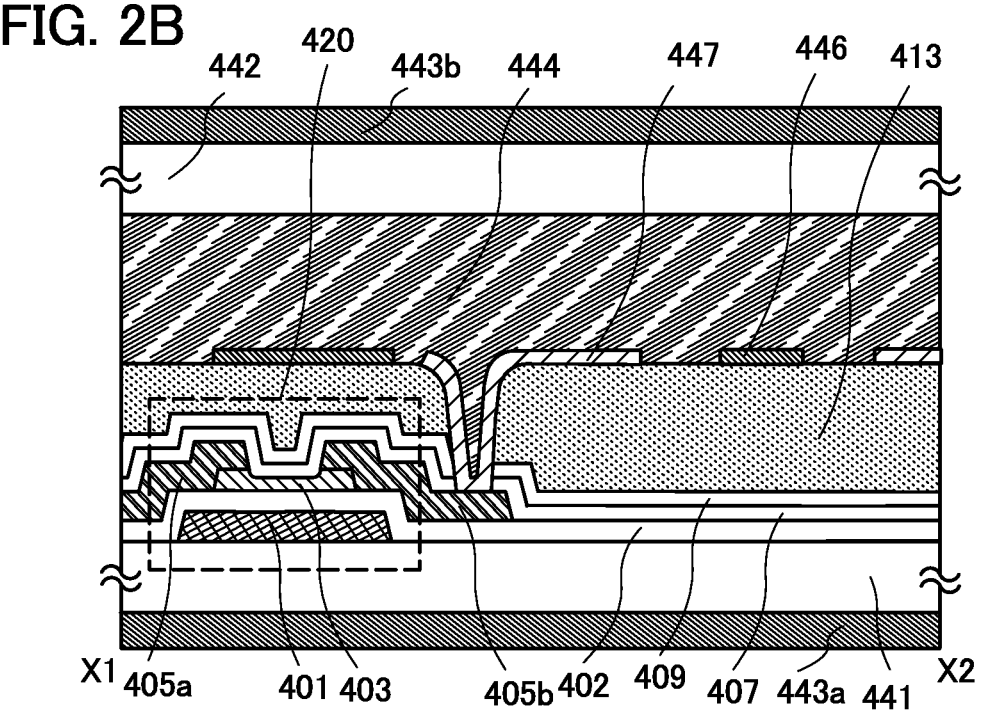

FIG. 2A is a plan view of the liquid crystal display device and illustrates one pixel. FIG. 2B is a cross-sectional view taken along line X1-X2 in FIG. 2A.

In FIG. 2A, a plurality of source wiring layers (including a wiring layer 405a) is arranged so as to be parallel to (extend in the vertical direction in the drawing) and apart from each other. A plurality of gate wiring layers (including a gate electrode layer 401) is provided to extend in a direction generally perpendicular to the source wiring layers (the horizontal direction in the drawing) and to be apart from each other. Common wiring layers 408 are provided adjacent to the respective plurality of gate wiring layers and extend in a direction generally parallel to the gate wiring layers, that is, in a direction generally perpendicular to the source wiring layers (the horizontal direction in the drawing). A roughly rectangular space is surrounded by the source wiring layers, the common wiring layers 408, and the gate wiring layers. In this space, a pixel electrode layer and a common electrode layer of the liquid crystal display device are provided. A transistor 420 for driving the pixel electrode layer is provided at an upper left corner of the drawing. A plurality of pixel electrode layers and a plurality of transistors are arranged in matrix.

In the liquid crystal display device of FIGS. 2A and 2B, a first electrode layer 447 which is electrically connected to the transistor 420 serves as a pixel electrode layer, while a second electrode layer 446 which is electrically connected to the common electrode layer 408 serves as a common electrode layer. Note that a capacitor is formed by the first electrode layer and the common wiring layer. Although the common electrode layer can operate in a floating state (an electrically isolated state), the potential of the common electrode layer may be set to a fixed potential, preferably to a potential around a common potential (an intermediate potential of an image signal which is transmitted as data) in such a level as not to generate flickers.

A method in which the gray scale is controlled by generating an electric field generally parallel (i.e., in a lateral direction) to a substrate to move liquid crystal molecules in a plane parallel to the substrate can be used. For such a method, an electrode structure used in an IPS mode as illustrated in FIGS. 2A and 2B and FIGS. 3A to 3D can be employed.

In a lateral electric field mode such as an IPS mode, a first electrode layer (e.g., a pixel electrode layer a voltage of which is controlled in each pixel) and a second electrode layer (e.g., a common electrode layer to which a common voltage is supplied in all pixels), each of which has an opening pattern, are located below a liquid crystal composition. Therefore, the first electrode layer 447 and the second electrode layer 446, one of which is a pixel electrode layer and the other of which is a common electrode layer, are formed over a first substrate 441, and at least one of the first electrode layer and the second electrode layer is formed over an insulating film. The first electrode layer 447 and the second electrode layer 446 have not a plane shape but various opening patterns including a bent portion or a comb-shaped portion. The first electrode layer 447 and the second electrode layer 446 do not have the same shape or do not overlap with each other in order to generate an electric field between the electrodes.

The first electrode layer 447 and the second electrode layer 446 may have an electrode structure used in an FFS mode. In a lateral electric field mode such as an FFS mode, a first electrode layer (e.g., a pixel electrode layer a voltage of which is controlled in each pixel) having an opening pattern is located below a liquid crystal composition, and further, a second electrode layer (e.g., a common electrode layer to which a common voltage is supplied in all pixels) having a flat shape is located below the opening pattern. In this case, the first electrode layer and the second electrode layer, one of which is a pixel electrode layer and the other of which is a common electrode layer, are formed over the first substrate 441, and the pixel electrode layer and the common electrode layer are stacked with an insulating film (or an interlayer insulating layer) interposed therebetween. One of the pixel electrode layer and the common electrode layer is formed below the insulating film (or the interlayer insulating layer) and has a flat shape, whereas the other is formed above the insulating film (or the interlayer insulating layer) and has various opening patterns including a bent portion or a branched comb-like portion. The first electrode layer 447 and the second electrode layer 446 do not have the same shape or do not overlap with each other in order to generate an electric field between the electrodes.

The liquid crystal composition including the dioxolane compound represented by the general formula (G1) shown in Embodiment 1 and a nematic liquid crystal is used as a liquid crystal composition 444. The liquid crystal composition 444 may further include an organic resin. In this embodiment, the liquid crystal composition including the dioxolane compound represented by the general formula (G1) and a nematic liquid crystal and exhibiting a blue phase is used as the liquid crystal composition 444. The liquid crystal composition 444 is provided in a liquid crystal display device with a blue phase exhibited (with a blue phase shown) by being subjected to polymer stabilization treatment.

With an electric field generated between the first electrode layer 447 as the pixel electrode layer and the second electrode layer 446 as the common electrode layer, liquid crystal of the liquid crystal composition 444 is controlled. An electric field in a lateral direction is formed for the liquid crystal, so that liquid crystal molecules can be controlled using the electric field. That is, the liquid crystal molecules aligned to exhibit a blue phase can be controlled in the direction parallel to the substrate, whereby a wide viewing angle can be obtained.

Figure 3A:
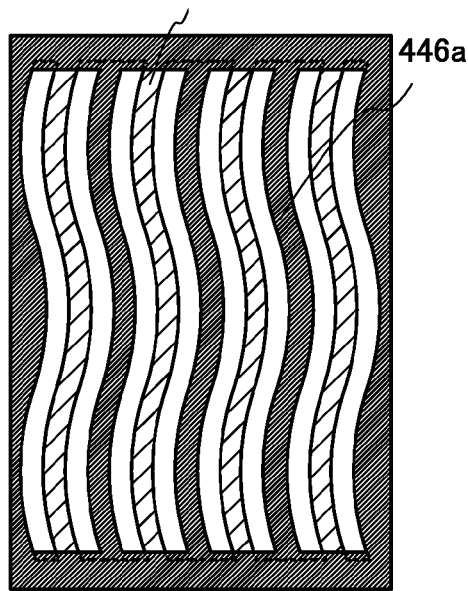
FIGS. 3A to 3D each illustrate one mode of an electrode structure of a liquid crystal display device.
Figure 3B:
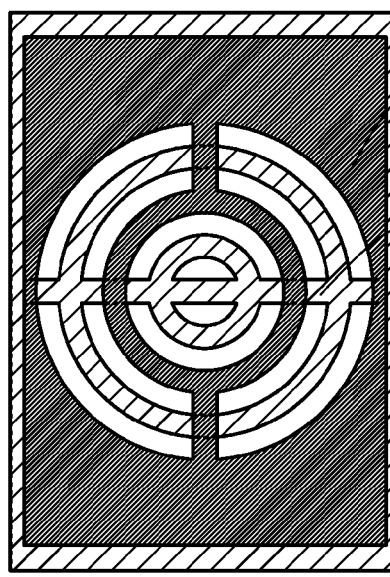
Figure 3C:
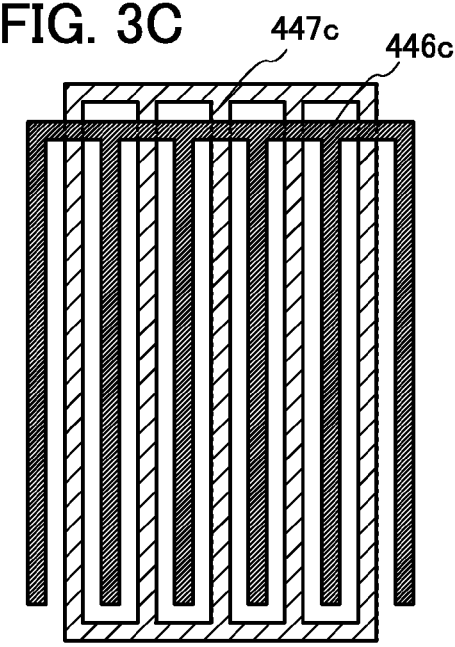
Figure 3D:
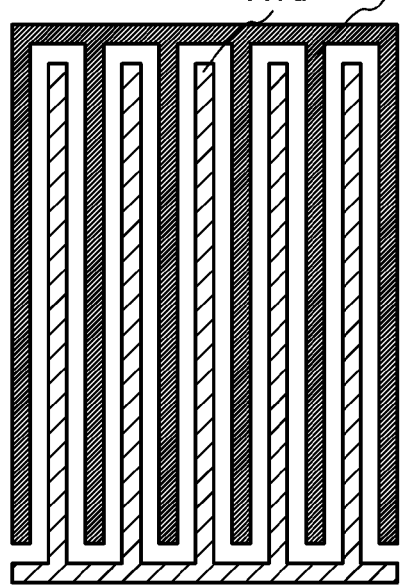

FIGS. 3A to 3D show other examples of the first electrode layer 447 and the second electrode layer 446. As illustrated in top views of FIGS. 3A to 3D, first electrode layers 447a to 447d and second electrode layers 446a to 446d are arranged alternately. In FIG. 3A, the first electrode layer 447a and the second electrode layer 446a have a wavelike shape with curves. In FIG. 3B, the first electrode layer 447b and the second electrode layer 446b have a shape with concentric circular openings. In FIG. 3C, the first electrode layer 447c and the second electrode layer 446c have a comb-shape and partially overlap with each other. In FIG. 3D, the first electrode layer 447d and the second electrode layer 446d have a comb-shape in which the electrode layers are engaged with each other. In the case where the first electrode layers 447a, 447b, and 447c overlap with the second electrode layers 446a, 446b, and 446c, respectively, as illustrated in FIGS. 3A to 3C, an insulating film is formed between the first electrode layer 447 and the second electrode layer 446 so that the first electrode layer 447 and the second electrode layer 446 are formed over different films.

Since the first electrode layer 447 and the second electrode layer 446 have an opening pattern, they are illustrated as divided plural electrode layers in the cross-sectional view of FIG. 2B. The same applies to the other drawings of this specification.

The transistor 420 is an inverted staggered thin film transistor in which the gate electrode layer 401, a gate insulating layer 402, a semiconductor layer 403, and wiring layers 405a and 405b which function as a source electrode layer and a drain electrode layer are formed over the first substrate 441 which has an insulating surface.

There is no particular limitation on a structure of a transistor which can be used for a liquid crystal display device disclosed in this specification. For example, a staggered type or a planar type having a top-gate structure or a bottom-gate structure can be employed. The transistor may have a single-gate structure in which one channel formation region is formed, a double-gate structure in which two channel formation regions are formed, or a triple-gate structure in which three channel formation regions are formed. Alternatively, the transistor may have a dual gate structure including two gate electrode layers positioned over and below a channel region with a gate insulating layer provided therebetween.

An insulating film 407 which is in contact with the semiconductor layer 403, and an insulating film 409 are provided to cover the transistor 420. An interlayer film 413 is stacked over the insulating film 409.

There is no particular limitation on the method for forming the interlayer film 413, and any of the following method can be employed depending on the material: spin coating, dip coating, spray coating, a droplet discharging method (such as an ink-jet method), screen printing, offset printing, roll coating, curtain coating, knife coating, and the like.

The first substrate 441 and a second substrate 442 which is a counter substrate are firmly attached to each other with a sealant with the liquid crystal composition 444 interposed therebetween. The liquid crystal composition 444 can be formed by a dispenser method (a dropping method), or an injection method by which a liquid crystal is injected using capillary action or the like after the first substrate 441 is attached to the second substrate 442.

As the sealant, typically, a visible light curable resin, a UV curable resin, or a thermosetting resin is preferably used. Typically, an acrylic resin, an epoxy resin, an amine resin, or the like can be used. Further, a photopolymerization initiator (typically, an ultraviolet light polymerization initiator), a thermosetting agent, a filler, or a coupling agent may be included in the sealant.

When a liquid crystal composition including a photopolymerization initiator, a polymerizable monomer, the dioxolane compound represented by the general formula (G1), and a nematic liquid crystal is used as the liquid crystal composition 444, polymer stabilization treatment can be performed by light irradiation.

After the space between the first substrate 441 and the second substrate 442 is filled with the liquid crystal composition, polymer stabilization treatment is performed by light irradiation, whereby the liquid crystal composition 444 is formed. The light has a wavelength at which the polymerizable monomer and the photopolymerization initiator which are included in the liquid crystal composition that is used as the liquid crystal composition 444 react. By such polymer stabilization treatment by light irradiation, the temperature range within which the liquid crystal composition 444 exhibits a blue phase can be broadened.

In the case where a photocurable resin such as a UV curable resin is used as a sealant and a liquid crystal composition is formed by a dropping method, for example, the sealant may be cured in the light irradiation step of the polymer stabilization treatment.

In this embodiment, a polarizing plate 443a is provided on the outer side (on the side opposite to the liquid crystal composition 444) of the first substrate 441, and a polarizing plate 443b is provided on the outer side (on the side opposite to the liquid crystal composition 444) of the second substrate 442. In addition to the polarizing plates, an optical film such as a retardation plate or an anti-reflection film may be provided. For example, circular polarization by the polarizing plate and the retardation plate may be used. Through the above-described process, a liquid crystal display device can be completed.

In the case of manufacturing a plurality of liquid crystal display devices using a large substrate (a so-called multiple panel method), a division step can be performed before the polymer stabilization treatment or before provision of the polarizing plates. In consideration of the influence of the division step on the liquid crystal composition (such as alignment disorder due to force applied in the division step), it is preferable that the division step be performed after attaching the first substrate and the second substrate and before performing the polymer stabilization treatment.

Although not illustrated, a backlight, a sidelight, or the like may be used as a light source. Light from the light source is emitted from the side of the first substrate 441 which is an element substrate so as to pass through the second substrate 442 on the viewing side.

The first electrode layer 447 and the second electrode layer 446 can be formed using a light-transmitting conductive material such as indium oxide containing tungsten oxide, indium zinc oxide containing tungsten oxide, indium oxide containing titanium oxide, indium tin oxide containing titanium oxide, indium tin oxide (hereinafter referred to as ITO), indium zinc oxide, indium tin oxide to which silicon oxide is added, or graphene.

The first electrode layer 447 and the second electrode layer 446 can be formed using one kind or plural kinds selected from a metal such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), or silver (Ag); an alloy thereof; and a nitride thereof.

A conductive composition containing a conductive high molecule (also referred to as a conductive polymer) can be used to form the first electrode layer 447 and the second electrode layer 446. The pixel electrode formed using the conductive composition preferably has a sheet resistance of less than or equal to 10000 ohms per square and a transmittance of greater than or equal to 70% at a wavelength of 550 nm. Further, the resistivity of the conductive high molecule included in the conductive composition is preferably less than or equal to 0.1 $\Omega \cdot cm$.

As the conductive high molecule, a so-called $\pi$-electron conjugated conductive polymer can be used. Examples include polyaniline or a derivative thereof, polypyrrole or a derivative thereof, polythiophene or a derivative thereof, and a copolymer of two or more of aniline, pyrrole, and thiophene or a derivative thereof.

An insulating film serving as a base film may be provided between the first substrate 441 and the gate electrode layer 401. The base film has a function of preventing diffusion of an impurity element from the first substrate 441, and can be formed to have a single-layer structure or a layered structure using one or more selected from a silicon nitride film, a silicon oxide film, a silicon nitride oxide film, and a silicon oxynitride film. The gate electrode layer 401 can be formed to have a single-layer or layered structure using a metal material such as molybdenum, titanium, chromium, tantalum, tungsten, aluminum, copper, neodymium, or scandium, or an alloy material which contains any of these materials as its main component. A semiconductor film which is doped with an impurity element such as phosphorus and is typified by a polycrystalline silicon film, or a silicide film of nickel silicide or the like can also be used as the gate electrode layer 401. By using a light-blocking conductive film as the gate electrode layer 401, light from a backlight (light emitted through the first substrate 441) can be prevented from entering the semiconductor layer 403.

For example, as a two-layer structure of the gate electrode layer 401, the following structures are preferable: a two-layer structure of an aluminum layer and a molybdenum layer stacked thereover, a two-layer structure of a copper layer and a molybdenum layer stacked thereover, a two-layer structure of a copper layer and a titanium nitride layer or a tantalum nitride layer stacked thereover, and a two-layer structure of a titanium nitride layer and a molybdenum layer. As a three-layer structure, a layered structure in which a tungsten layer or a tungsten nitride layer, an alloy layer of aluminum and silicon or an alloy layer of aluminum and titanium, and a titanium nitride layer or a titanium layer are stacked is preferable.

For example, the gate insulating layer 402 can be formed by a plasma CVD method or a sputtering method, with the use of a silicon oxide film, a gallium oxide film, an aluminum oxide film, a silicon nitride film, a silicon oxynitride film, an aluminum oxynitride film, or a silicon nitride oxide film. Alternatively, a high-k material such as hafnium oxide, yttrium oxide, lanthanum oxide, hafnium silicate, hafnium aluminate, hafnium silicate to which nitrogen is added, or hafnium aluminate to which nitrogen is added may be used as a material for the gate insulating layer 402. The use of such a high-k material enables a reduction in gate leakage current.

Alternatively, the gate insulating layer 402 can be formed using a silicon oxide layer by a CVD method in which an organosilane gas is used. As an organosilane gas, a silicon-containing compound such as tetraethoxysilane (TEOS) (chemical formula: $Si(OC_2H_5)_4$), tetramethylsilane (TMS) (chemical formula: $Si(CH_3)_4$), tetramethylcyclotetrasiloxane (TMCTS), octamethylcyclotetrasiloxane (OMCTS), hexamethyldisilazane (HMDS), triethoxysilane (chemical formula: SiH(OC$_2$H$_5$)$_3$), or trisdimethylaminosilane (chemical formula: SiH(N(CH$_3$)$_2$)$_3$) can be used. Note that the gate insulating layer 402 may have a single layer structure or a layered structure.

A material of the semiconductor layer 403 is not limited to a particular material and may be determined in accordance with characteristics needed for the transistor 420, as appropriate. Examples of a material which can be used for the semiconductor layer 403 will be described.

The semiconductor layer 403 can be formed using the following material: an amorphous semiconductor manufactured by a sputtering method or a vapor-phase growth method using a semiconductor source gas typified by silane or germane; a polycrystalline semiconductor formed by crystallizing the amorphous semiconductor with the use of light energy or thermal energy; a microcrystalline semiconductor; or the like. The semiconductor layer can be formed by a sputtering method, an LPCVD method, a plasma CVD method, or the like.

A typical example of an amorphous semiconductor is hydrogenated amorphous silicon, while a typical example of a crystalline semiconductor is polysilicon and the like. Polysilicon (polycrystalline silicon) includes so-called high-temperature polysilicon that contains, as its main component, polysilicon formed at a process temperature of 800° C. or higher, so-called low-temperature polysilicon that contains, as its main component, polysilicon formed at a process temperature of 600° C. or lower, and polysilicon formed by crystallizing amorphous silicon by using an element which promotes crystallization, or the like. Needless to say, as described above, a microcrystalline semiconductor or a semiconductor which includes a crystal phase in part of a semiconductor layer can also be used.

Alternatively, an oxide semiconductor may be used. In that case, any of the following can be used: indium oxide; tin oxide; zinc oxide; a two-component metal oxide such as an In—Zn-based oxide, a Sn—Zn-based oxide, an Al—Zn-based oxide, a Zn—Mg-based oxide, a Sn—Mg-based oxide, an In—Mg-based oxide, or an In—Ga-based oxide; a three-component metal oxide such as an In—Ga—Zn-based oxide (also referred to as IGZO), an In—Al—Zn-based oxide, an In—Sn—Zn-based oxide, a Sn—Ga—Zn-based oxide, an Al—Ga—Zn-based oxide, a Sn—Al—Zn-based oxide, an In—Hf—Zn-based oxide, an In—La—Zn-based oxide, an In—Ce—Zn-based oxide, an In—Pr—Zn-based oxide, an In—Nd—Zn-based oxide, an In—Sm—Zn-based oxide, an In—Eu—Zn-based oxide, an In—Gd—Zn-based oxide, an In—Tb—Zn-based oxide, an In—Dy—Zn-based oxide, an In—Ho—Zn-based oxide, an In—Er—Zn-based oxide, an In—Tm—Zn-based oxide, an In—Yb—Zn-based oxide, or an In—Lu—Zn-based oxide; and a four-component metal oxide such as an In—Sn—Ga—Zn-based oxide, an In—Hf—Ga—Zn-based oxide, an In—Al—Ga—Zn-based oxide, an In—Sn—Al—Zn-based oxide, an In—Sn—Hf—Zn-based oxide, or an In—Hf—Al—Zn-based oxide. In addition, any of the above oxide semiconductors may contain an element other than In, Ga, Sn, and Zn, for example, SiO$_2$.

Here, for example, an In—Ga—Zn—O-based oxide semiconductor means an oxide semiconductor containing indium (In), gallium (Ga), and zinc (Zn), and there is no limitation on the composition thereof.

For the oxide semiconductor layer, a thin film expressed by a chemical formula of InMO$_3$(ZnO)$_m$ (m>0) can be used. Here, M denotes one or more metal elements selected from Ga, Al, Mn, and Co. For example, Ga, Ga and Al, Ga and Mn, or Ga and Co can be given as M.

In the case where an In—Sn—Zn—O-based oxide semiconductor material is used as an oxide semiconductor, a target therefor may have a composition of In:Sn:Zn=1:2:2, In:Sn:Zn=2:1:3, or In:Sn:Zn=1:1:1 in an atomic ratio, for example.

In the case where an In—Zn—O-based material is used as the oxide semiconductor, the atomic ratio thereof is In/Zn=0.5 to 50, preferably In/Zn=1 to 20, more preferably In/Zn=1.5 to 15. When the atomic ratio of Zn is in the above preferred range, the field-effect mobility of a transistor can be improved. Here, when the atomic ratio of the compound is In:Zn:O=X:Y:Z, the relation Z>1.5X+Y is satisfied.

As the oxide semiconductor layer, a CAAC-OS (c-axis aligned crystalline oxide semiconductor) film which is neither completely single crystal nor completely amorphous can be used. The CAAC-OS film is an oxide semiconductor film with a crystal-amorphous mixed phase structure where crystal parts are included in an amorphous phase. In the crystal portion included in the CAAC-OS film, c-axes are aligned in the direction parallel (including the range of −5° to 5°) to a normal vector of the surface where the CAAC-OS film is formed or a normal vector of the surface of the CAAC-OS film, a triangular or hexagonal atomic arrangement is provided when seen from the direction perpendicular to an a-b plane, and metal atoms are arranged in a layered manner or metal atoms and oxygen atoms are arranged in a layered manner when seen from the direction perpendicular (including the range of 85° to 95°) to the c-axis. Note that, among crystal parts, the directions of the a-axis and the b-axis of one crystal part may be different from those of another crystal part.

In a process of forming the semiconductor layer and the wiring layer, an etching step is used to process thin films into desired shapes. Dry etching or wet etching can be used for the etching step.

The etching conditions (such as an etchant, etching time, and temperature) are appropriately adjusted depending on the material so that the material can be etched into a desired shape.

As a material of the wiring layers 405a and 405b serving as source and drain electrode layers, an element selected from Al, Cr, Ta, Ti, Mo, and W; an alloy containing any of the above elements as its component; an alloy film containing a combination of any of these elements; and the like can be given. Further, in the case where heat treatment is performed, the conductive film preferably has heat resistance against the heat treatment. Since use of Al alone brings disadvantages such as low heat resistance and a tendency to corrosion, aluminum is used in combination with a conductive material having heat resistance. As the conductive material having heat resistance, which is combined with aluminum, it is possible to use an element selected from titanium (Ti), tantalum (Ta), tungsten (W), molybdenum (Mo), chromium (Cr), neodymium (Nd), and scandium (Sc); an alloy containing any of these elements as its component; an alloy containing a combination of any of these elements; or a nitride containing any of these elements as its component.

The gate insulating layer 402, the semiconductor layer 403, and the wiring layers 405a and 405b serving as source and drain electrode layers may be successively formed without being exposed to the air. When the gate insulating layer 402, the semiconductor layer 403, and the wiring layers 405a and 405b are formed successively without being exposed to the air, an interface between the layers can be formed without being contaminated with atmospheric components or impurity elements contained in the air. Thus, variations in characteristics of thin film transistors can be reduced.

Note that the semiconductor layer 403 is partly etched so as to have a groove (a depressed portion).

As the insulating film 407 and the insulating film 409 which cover the transistor 420, an inorganic insulating film or an organic insulating film formed by a dry method or a wet method can be used. For example, it is possible to use a silicon nitride film, a silicon oxide film, a silicon oxynitride film, an aluminum oxide film, or a tantalum oxide film, which is formed by a CVD method, a sputtering method, or the like. Alternatively, an organic material such as polyimide, acrylic, benzocyclobutene, polyamide, or an epoxy resin can be used. Other than such organic materials, it is also possible to use a low-dielectric constant material (a low-k material), a siloxane-based resin, PSG (phosphosilicate glass), BPSG (borophosphosilicate glass), or the like. A gallium oxide film may also be used as the insulating film 407.

Note that the siloxane-based resin corresponds to a resin including a Si—O—Si bond formed using a siloxane-based material as a starting material. The siloxane-based resin may include as a substituent an organic group (e.g., an alkyl group or an aryl group) or a fluoro group. In addition, the organic group may include a fluoro group. A siloxane-based resin is applied by a coating method and baked; thus, the insulating film 407 can be formed.

Alternatively, the insulating film 407 and the insulating film 409 may be formed by stacking a plurality of insulating films formed using any of these materials. For example, the insulating film 407 and the insulating film 409 may each have such a structure that an organic resin film is stacked over an inorganic insulating film.

Further, with the use of a resist mask having regions with plural thicknesses (typically, two different thicknesses) which is formed using a multi-tone mask, the number of resist masks can be reduced, resulting in simplified process and lower costs.

In the above manner, by using the liquid crystal composition including the dioxolane compound represented by the general formula (G1) and a nematic liquid crystal for a liquid crystal element or a liquid crystal display device, a liquid crystal element or liquid crystal display device that can be driven at a low driving voltage can be provided. Thus, a reduction in power consumption of the liquid crystal display device can be achieved.

Further, the liquid crystal composition including the dioxolane compound represented by the general formula (G1) and a nematic liquid crystal and exhibiting a blue phase is capable of quick response. Thus, by using the liquid crystal composition for a liquid crystal display device, a high-performance liquid crystal display device can be provided.

The structures, methods, and the like described in this embodiment can be combined as appropriate with any of the other structures, methods, and the like described in the other embodiments.

Embodiment 4

A liquid crystal display device having a display function can be manufactured by manufacturing transistors and using the transistors in a pixel portion and further in a driver circuit. Further, part or the whole of the driver circuit can be formed over the same substrate as the pixel portion, using the transistor, whereby a system-on-panel can be obtained.

The liquid crystal display device includes a liquid crystal element (also referred to as a liquid crystal display element) as a display element.

Further, a liquid crystal display device includes a panel in which a display element is sealed, and a module in which an IC or the like including a controller is mounted to the panel. One embodiment of the present invention also relates to an element substrate, which corresponds to one mode before the display element is completed in a manufacturing process of the liquid crystal display device, and the element substrate is provided with a means for supplying current to the display element in each of a plurality of pixels. Specifically, the element substrate may be in a state in which only a pixel electrode of the display element is provided, a state after formation of a conductive film to be a pixel electrode and before etching of the conductive film to form the pixel electrode, or any other states.

Note that a liquid crystal display device in this specification means an image display device, a display device, or a light source (including a lighting device). Further, a liquid crystal display device also refers to all the following modules: a module to which a connector, for example, an FPC (flexible printed circuit), a TAB (tape automated bonding) tape, or a TCP (tape carrier package) is attached, a module in which a printed wiring board is provided at an end of a TAB tape or a TCP, and a module in which an IC (integrated circuit) is directly mounted on a display element by a COG (chip on glass) method.

The appearance and a cross section of a liquid crystal display panel which corresponds to a liquid crystal display device of one embodiment of the present invention will be described with reference to FIGS. 4A1 and 4A2 and 4B. FIGS. 4A1 and 4A2 are top views of a panel in which transistors 4010 and 4011 and a liquid crystal element 4013 which are formed over a first substrate 4001 are sealed between the first substrate 4001 and a second substrate 4006 with a sealant 4005. FIG. 4B is a cross-sectional view taken along M-N of FIGS. 4A1 and 4A2.

The sealant 4005 is provided so as to surround a pixel portion 4002 and a scan line driver circuit 4004 which are provided over the first substrate 4001. The second substrate 4006 is provided over the pixel portion 4002 and the scan line driver circuit 4004. Thus, the pixel portion 4002 and the scan line driver circuit 4004 are sealed together with a liquid crystal composition 4008, by the first substrate 4001, the sealant 4005, and the second substrate 4006.

In FIG. 4A1, a signal line driver circuit 4003 that is formed using a single crystal semiconductor film or a polycrystalline semiconductor film over a substrate separately prepared is mounted in a region that is different from the region surrounded by the sealant 4005 over the first substrate 4001. FIG. 4A2 illustrates an example in which part of a signal line driver circuit is formed with the use of a transistor which is provided over the first substrate 4001. A signal line driver circuit 4003b is formed over the first substrate 4001 and a signal line driver circuit 4003a which is formed using a single crystal semiconductor film or a polycrystalline semiconductor film is mounted over a substrate separately prepared.

Note that there is no particular limitation on the connection method of a driver circuit which is separately formed, and a COG method, a wire bonding method, a TAB method, or the like can be used. FIG. 4A1 illustrates an example of mounting the signal line driver circuit 4003 by a COG method, and FIG. 4A2 illustrates an example of mounting the signal line driver circuit 4003 by a TAB method.

The pixel portion 4002 and the scan line driver circuit 4004 provided over the first substrate 4001 include a plurality of transistors. FIG. 4B illustrates the transistor 4010 included in the pixel portion 4002 and the transistor 4011 included in the scan line driver circuit 4004, as an example. An insulating layer 4020 and an interlayer film 4021 are provided over the transistors 4010 and 4011.

Any of the transistors shown in Embodiment 3 can be used as the transistors 4010 and 4011.

Further, a conductive layer may be provided over the interlayer film 4021 or the insulating layer 4020 so as to overlap with a channel formation region of a semiconductor layer of the transistor 4011 for the driver circuit. The conductive layer may have the same potential as or a potential different from that of a gate electrode layer of the transistor 4011 and can function as a second gate electrode layer. Further, the potential of the conductive layer may be GND or 0 V, or the conductive layer may be in a floating state.

A pixel electrode layer 4030 and a common electrode layer 4031 are provided over the interlayer film 4021, and the pixel electrode layer 4030 is electrically connected to the transistor 4010. The liquid crystal element 4013 includes the pixel electrode layer 4030, the common electrode layer 4031, and the liquid crystal composition 4008. Note that a polarizing plate 4032*a* and a polarizing plate 4032*b* are provided on the outer sides of the first substrate 4001 and the second substrate 4006, respectively.

A liquid crystal composition including the dioxolane compound represented by the general formula (G1) shown in Embodiment 1 and a nematic liquid crystal is used as the liquid crystal composition 4008. The structures of the pixel electrode layer and the common electrode layer described in any of the above embodiments can be used for the pixel electrode layer 4030 and the common electrode layer 4031.

In this embodiment, the liquid crystal composition including the dioxolane compound represented by the general formula (G1) and a nematic liquid crystal and exhibiting a blue phase is used as the liquid crystal composition 4008. The liquid crystal composition 4008 is provided in a liquid crystal display device with a blue phase exhibited (with a blue phase shown) by being subjected to polymer stabilization treatment. Therefore, in this embodiment, the pixel electrode layer 4030 and the common electrode layer 4031 have opening patterns illustrated in FIG. 1A described in Embodiment 2 or FIGS. 3A to 3D described in Embodiment 3.

With an electric field generated between the pixel electrode layer 4030 and the common electrode layer 4031, liquid crystal of the liquid crystal composition 4008 is controlled. An electric field in a lateral direction is formed for the liquid crystal, so that liquid crystal molecules can be controlled using the electric field. That is, the liquid crystal molecules aligned to exhibit a blue phase can be controlled in a direction parallel to the substrate, whereby a wide viewing angle is obtained.

As the first substrate 4001 and the second substrate 4006, glass, plastic, or the like having a light-transmitting property can be used. As plastic, a fiberglass-reinforced plastics (FRP) plate, a poly(vinyl fluoride) (PVF) film, a polyester film, or an acrylic resin film can be used. In addition, a sheet with a structure in which an aluminum foil is interposed between PVF films or polyester films can be used.

A columnar spacer denoted by reference numeral 4035 is obtained by selective etching of an insulating film and is provided in order to control the thickness (a cell gap) of the liquid crystal composition 4008. Alternatively, a spherical spacer may also be used. In the liquid crystal display device including the liquid crystal composition 4008, the cell gap which is the thickness of the liquid crystal composition is preferably greater than or equal to 1 µm and less than or equal to 20 µm. In this specification, the thickness of a cell gap refers to the length (film thickness) of a thickest part of a liquid crystal composition.

Although FIGS. 4A1, 4A2, and 4B illustrate examples of transmissive liquid crystal display devices, one embodiment of the present invention can also be applied to a transflective liquid crystal display device and a reflective liquid crystal display device.

In the example of the liquid crystal display device illustrated in FIGS. 4A1, 4A2, and 4B, the polarizing plate is provided on the outer side (the viewing side) of the substrate; however, the polarizing plate may be provided on the inner side of the substrate. The position of the polarizing plate may be determined as appropriate depending on the material of the polarizing plate and conditions of the manufacturing process. Furthermore, a light-blocking layer serving as a black matrix may be provided.

A color filter layer or a light-blocking layer may be formed as part of the interlayer film 4021. In FIGS. 4A1, 4A2, and 4B, a light-blocking layer 4034 is provided on the second substrate 4006 side so as to cover the transistors 4010 and 4011. With the provision of the light-blocking layer 4034, the contrast can be increased and the transistors can be stabilized more.

The transistors may be, but is not necessarily, covered with the insulating layer 4020 which functions as a protective film of the transistors.

Note that the protective film is provided to prevent entry of contaminant impurities such as organic substance, metal, or moisture existing in the air and is preferably a dense film. The protective film may be formed by a sputtering method to have a single-layer structure or a layered structure including any of a silicon oxide film, a silicon nitride film, a silicon oxynitride film, a silicon nitride oxide film, an aluminum oxide film, an aluminum nitride film, an aluminum oxynitride film, and an aluminum nitride oxide film.

Further, in the case of further forming a light-transmitting insulating layer as a planarizing insulating film, the light-transmitting insulating layer can be formed using an organic material having heat resistance, such as polyimide, acrylic, benzocyclobutene, polyamide, or epoxy resin. Other than such organic materials, it is also possible to use a low-dielectric constant material (a low-k material), a siloxane-based resin, PSG (phosphosilicate glass), BPSG (borophosphosilicate glass), or the like. The insulating layer may be formed by stacking a plurality of insulating films formed using these materials.

There is no particular limitation on the method for forming the insulating layer having a layered structure, and the following method can be employed depending on the material: sputtering, spin coating, dip coating, spray coating, a droplet discharging method (such as an ink-jet method), screen printing, offset printing, roll coating, curtain coating, knife coating, or the like.

The pixel electrode layer 4030 and the common electrode layer 4031 can be formed using a light-transmitting conductive material such as indium oxide containing tungsten oxide, indium zinc oxide containing tungsten oxide, indium oxide containing titanium oxide, indium tin oxide containing titanium oxide, indium tin oxide (hereinafter referred to as ITO), indium zinc oxide, indium tin oxide to which silicon oxide is added, or graphene.

The pixel electrode layer 4030 and the common electrode layer 4031 can also be formed using one kind or plural kinds selected from a metal such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), or silver (Ag); an alloy thereof; and a nitride thereof.

Alternatively, the pixel electrode layer 4030 and the common electrode layer 4031 can be made using a conductive composition including a conductive high molecule (also referred to as a conductive polymer).

Further, a variety of signals and potentials are supplied to the signal line driver circuit 4003 which is separately formed, the scan line driver circuit 4004, or the pixel portion 4002 from an FPC 4018.

Further, since the transistor is easily broken by static electricity or the like, a protective circuit for protecting the driver circuits is preferably provided over the same substrate as a gate line or a source line. The protection circuit is preferably formed using a nonlinear element.

In FIGS. 4A1, 4A2, and 4B, a connection terminal electrode 4015 is formed using the same conductive film as that of the pixel electrode layer 4030, and a terminal electrode 4016 is formed using the same conductive film as that of source and drain electrode layers of the transistors 4010 and 4011.

The connection terminal electrode 4015 is electrically connected to a terminal included in the FPC 4018 via an anisotropic conductive film 4019.

Although FIGS. 4A1, 4A2, and 4B illustrate an example in which the signal line driver circuit 4003 is formed separately and mounted on the first substrate 4001, one embodiment of the present invention is not limited to this structure. The scan line driver circuit may be separately formed and then mounted, or only part of the signal line driver circuit or part of the scan line driver circuit may be separately formed and then mounted.

In the above manner, by using the liquid crystal composition including the dioxolane compound represented by the general formula (G1) and a nematic liquid crystal for a liquid crystal element or a liquid crystal display device, a liquid crystal element or liquid crystal display device that can be driven at a low driving voltage can be provided. Thus, a reduction in power consumption of the liquid crystal display device can be achieved.

Further, the liquid crystal composition including the dioxolane compound represented by the general formula (G1) and a nematic liquid crystal and exhibiting a blue phase is capable of quick response. Thus, by using the liquid crystal composition for a liquid crystal display device, a high-performance liquid crystal display device can be provided.

The structures, methods, and the like described in this embodiment can be combined as appropriate with any of the other structures, methods, and the like described in the other embodiments.

Embodiment 5

A liquid crystal display device disclosed in this specification can be used for a variety of electronic appliances (including game machines). Examples of such electronic appliances include a television set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a personal digital assistance, an audio reproducing device, a large game machine such as a pinball machine, and the like.

Figure 5A:
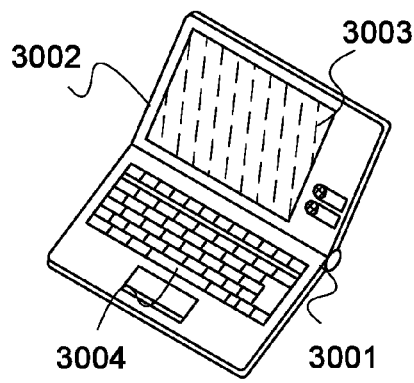
FIGS. 5A to 5F illustrate electronic appliances.

FIG. 5A illustrates a laptop personal computer, which includes a main body 3001, a housing 3002, a display portion 3003, a keyboard 3004, and the like. The liquid crystal display device described in any of the above Embodiments is used for the display portion 3003, whereby a laptop personal computer with low power consumption can be provided.

Figure 5B:
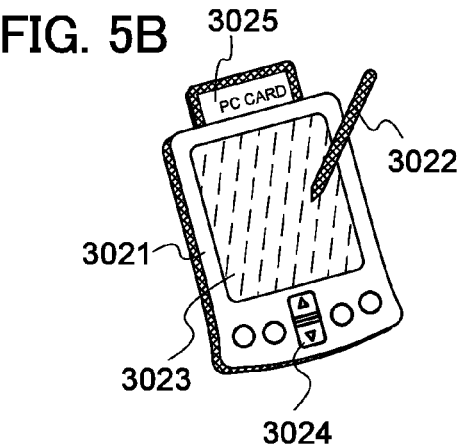

FIG. 5B illustrates a personal digital assistance (PDA), which includes a main body 3021 provided with a display portion 3023, an external interface 3025, operation buttons 3024, and the like. A stylus 3022 is included as an accessory for operation. The liquid crystal display device described in any of the above Embodiments is used for the display portion 3023, whereby a personal digital assistance (PDA) with low power consumption can be provided.

Figure 5C:
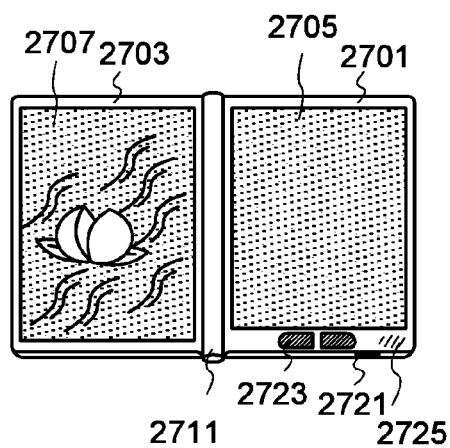

FIG. 5C illustrates an e-book reader, which includes two housings, a housing 2701 and a housing 2703. The housing 2701 and the housing 2703 are combined with a hinge 2711 so that the e-book reader can be opened and closed with the hinge 2711 as an axis. With such a structure, the e-book reader can operate like a paper book.

A display portion 2705 and a display portion 2707 are incorporated in the housing 2701 and the housing 2703, respectively. The display portion 2705 and the display portion 2707 may display one image or different images. In the structure where different images are displayed in the above display portions, for example, the right display portion (the display portion 2705 in FIG. 5C) can display text and the left display portion (the display portion 2707 in FIG. 5C) can display images. The liquid crystal display device described in any of the above Embodiments is used for the display portions 2705 and 2707, whereby an e-book reader with low power consumption can be provided. In the case of using a transflective or reflective liquid crystal display device for the display portion 2705, the e-book reader may be used in a comparatively bright environment; accordingly, a solar cell may be provided so that power generation by the solar cell and charge by a battery can be performed. When a lithium ion battery is used as the battery, there are advantages of downsizing and the like.

FIG. 5C illustrates an example in which the housing 2701 is provided with an operation portion and the like. For example, the housing 2701 is provided with a power switch 2721, operation keys 2723, a speaker 2725, and the like. With the operation key 2723, pages can be turned. Note that a keyboard, a pointing device, or the like may also be provided on the surface of the housing, on which the display portion is provided. Furthermore, an external connection terminal (an earphone terminal, a USB terminal, or the like), a recording medium insertion portion, and the like may be provided on the back surface or the side surface of the housing. Further, the e-book reader may have a function of an electronic dictionary.

The e-book reader may transmit and receive data wirelessly. Through wireless communication, desired book data or the like can be purchased and downloaded from an electronic book server.

Figure 5D:
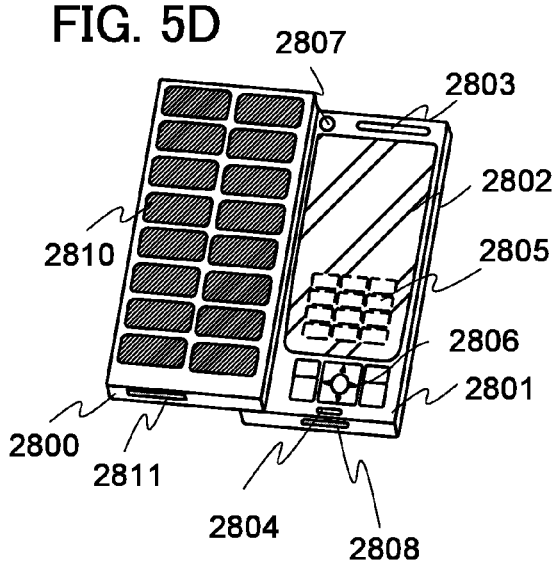

FIG. 5D illustrates a mobile phone, which includes two housings, a housing 2800 and a housing 2801. The housing 2801 includes a display panel 2802, a speaker 2803, a microphone 2804, a pointing device 2806, a camera lens 2807, an external connection terminal 2808, and the like. The housing 2800 includes a solar cell 2810 for charging the mobile phone, an external memory slot 2811, and the like. Further, an antenna is incorporated in the housing 2801. The liquid crystal display device described in any of the above Embodiments is used for the display panel 2802, whereby a mobile phone with low power consumption can be provided.

Further, the display panel 2802 is provided with a touch panel. A plurality of operation keys 2805 which is displayed as images is illustrated by dashed lines in FIG. 5D. Note that a boosting circuit by which a voltage output from the solar cell 2810 is increased to be sufficiently high for each circuit is also included.

In the display panel 2802, the display direction can be appropriately changed depending on a usage pattern. Further, the mobile phone is provided with the camera lens 2807 on the same surface as the display panel 2802, and thus it can be used as a video phone. The speaker 2803 and the microphone 2804 can be used for videophone calls, recording and playing sound, and the like as well as voice calls. Further, the housings 2800 and 2801 which are developed as illustrated in FIG. 5D can overlap with each other by sliding; thus, the size of the mobile phone can be decreased, which makes the mobile phone suitable for being carried.

The external connection terminal 2808 can be connected to an AC adapter and various types of cables such as a USB cable, and charging and data communication with a personal computer are possible. Moreover, a large amount of data can be stored and can be moved by inserting a storage medium into the external memory slot 2811.

Further, in addition to the above functions, an infrared communication function, a television reception function, or the like may be provided.

Figure 5E:
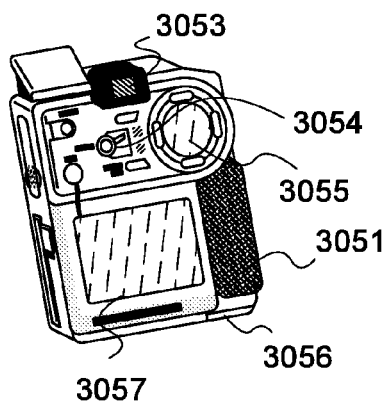

FIG. 5E illustrates a digital video camera, which includes a main body 3051, a display portion A 3057, an eyepiece 3053, an operation switch 3054, a display portion B 3055, a battery 3056, and the like. The liquid crystal display device described in any of the above Embodiments is used for the display portion A 3057 and the display portion B 3055, whereby a digital video camera with low power consumption can be provided.

Figure 5F:
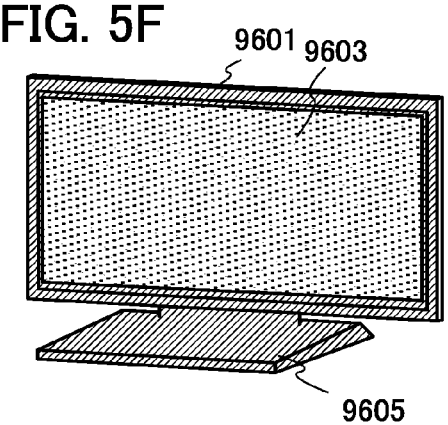

FIG. 5F illustrates a television device in which a display portion 9603 and the like are incorporated in a housing 9601. The display portion 9603 can display images. Here, the housing 9601 is supported by a stand 9605. The liquid crystal display device described in any of the above Embodiments is used for the display portion 9603, whereby a television device with low power consumption can be provided.

The television device can be operated with an operation switch of the housing 9601 or a separate remote controller. Further, the remote controller may be provided with a display portion for displaying data output from the remote controller.

Note that the television device is provided with a receiver, a modem, and the like. With the use of the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

The structures, methods, and the like described in this embodiment can be combined as appropriate with any of the other structures, methods, and the like described in the other embodiments.

Example 1

This example shows an example for synthesizing (4R,5R)-bis[benzyloxy-di(phenanthoren-9-yl)methyl]-2,2-dimethyl-1,3-dioxolane (abbreviation: R-DOL-Pn-O1Ph), which is a dioxolane compound represented by the structural formula (101) in Embodiment 1.

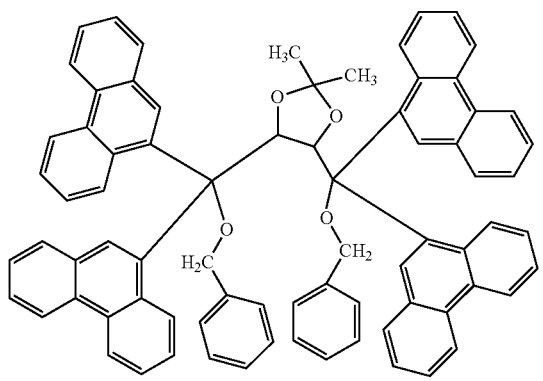

(101)

First, 2.5 g (2.9 mmol) of (4R,5R)-bis[hydroxy-di(phenanthoren-9-yl)methyl]-2,2-dimethyl-1,3-dioxolane, 1.1 g (6.4 mmol) of benzyl bromide, 0.90 g (6.4 mmol) of potassium carbonate, and 15 mL of cyclohexanol were put into a 50 mL recovery flask, and were stirred under a nitrogen stream at 140° C. for 3 hours. After predetermined time passed, water was added to the obtained mixture to extract an aqueous layer of this mixture with toluene. The obtained extract was washed with saturated saline together with the organic layer and then dried over magnesium sulfate. The mixture was gravity filtered, and the obtained filtrate was condensed to give a yellow solid.

This solid was purified by silica gel column chromatography (the developing solvent was toluene and then chloroform). The resulting fraction was condensed to give a white solid. This solid was purified by high performance liquid column chromatography (abbreviation: HPLC) (the developing solvent was chloroform).

The obtained fraction was condensed and dried in vacuum to give 1.6 g of the target white solid in a yield of 52%. The above synthesis scheme is shown in (E1) below.

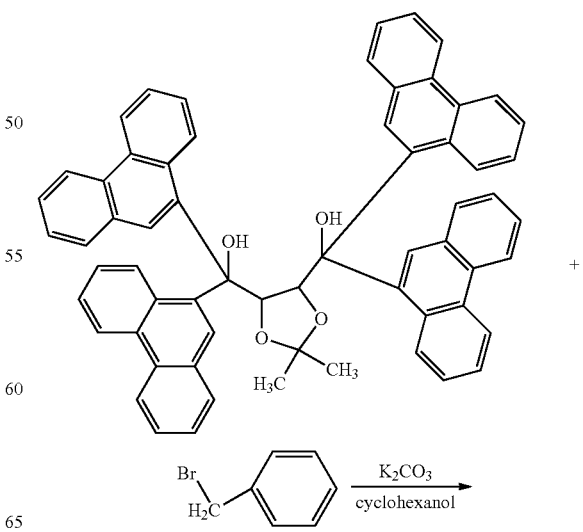

(E1)

-continued

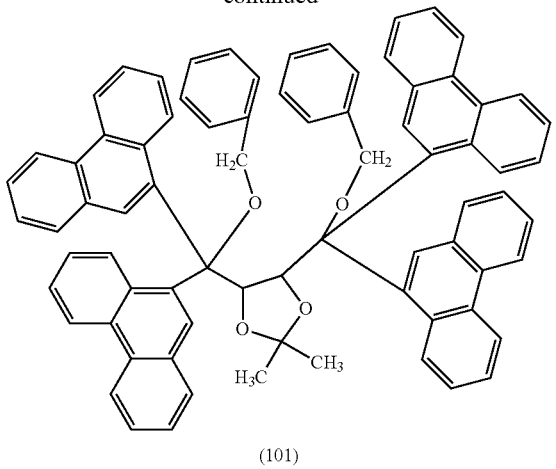

(101)

This compound was identified as the target (4R,5R)-bis[benzyloxy-di(phenanthoren-9-yl)methyl]-2,2-dimethyl-1,3-dioxolane (abbreviation: R-DOL-Pn-O1Ph) by nuclear magnetic resonance (NMR).

$^1$H-NMR data of the obtained substance (R-DOL-Pn-O1Ph) are as follows. $^1$H NMR (TCE, 300 MHz): δ (ppm)=1.02 (s, 4H), 1.35 (s, 6H), 4.11 (s, 2H), 5.91-8.72 (m, 46H).

Figure 6A:
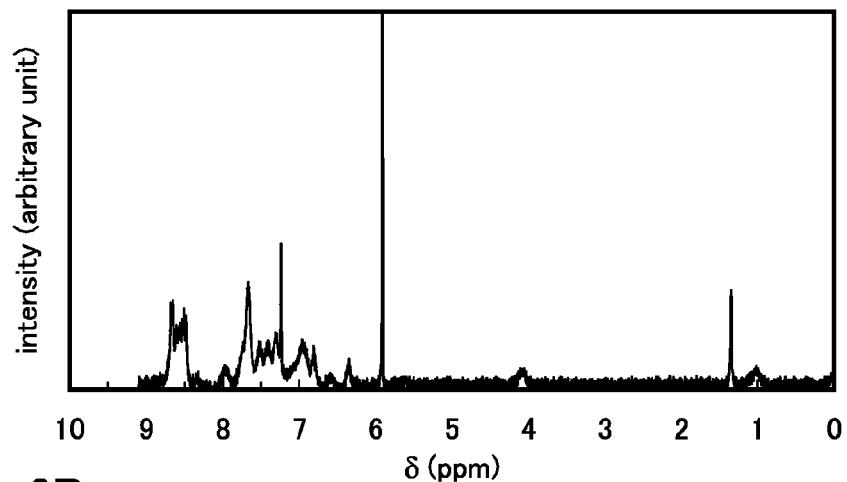
FIGS. 6A to 6C are NMR charts of R-DOL-Pn-O1Ph.
Figure 6B:
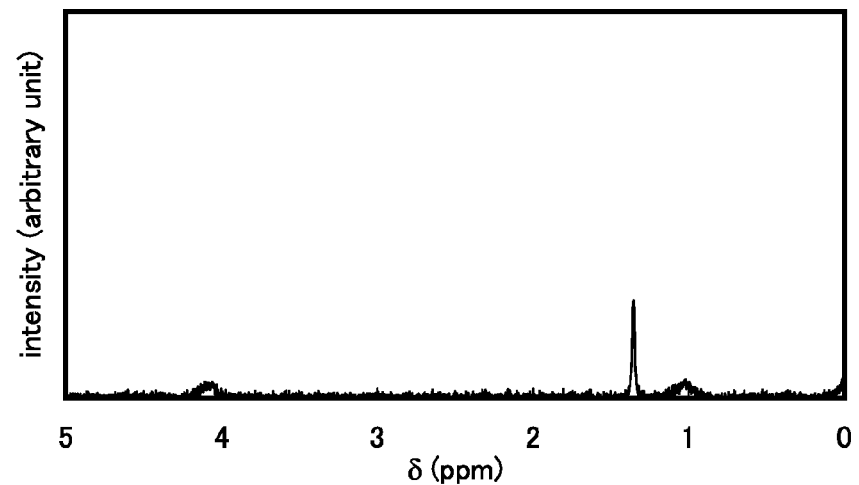
Figure 6C:
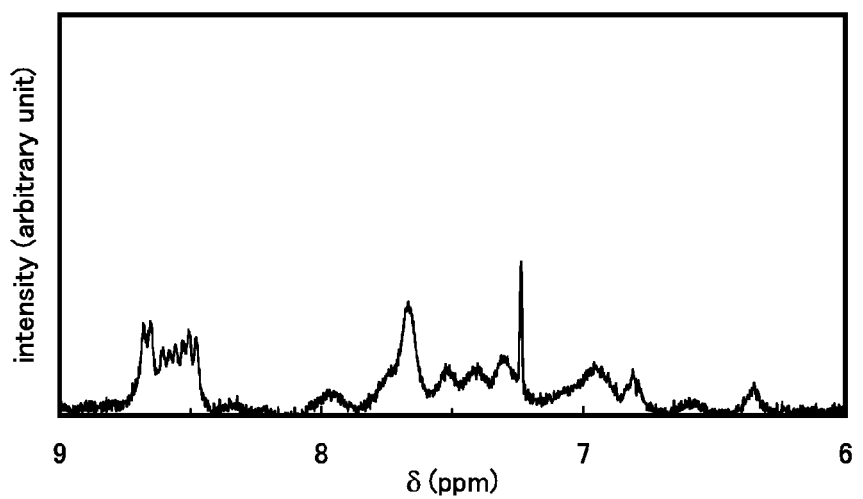

In addition, FIGS. 6A to 6C show $^1$H NMR charts. FIG. 6B is an enlarged chart showing a range of 0 ppm to 5 ppm of FIG. 6A, and FIG. 6C is an enlarged chart showing a range of 6 ppm to 9 ppm of FIG. 6A.

Figure 7:
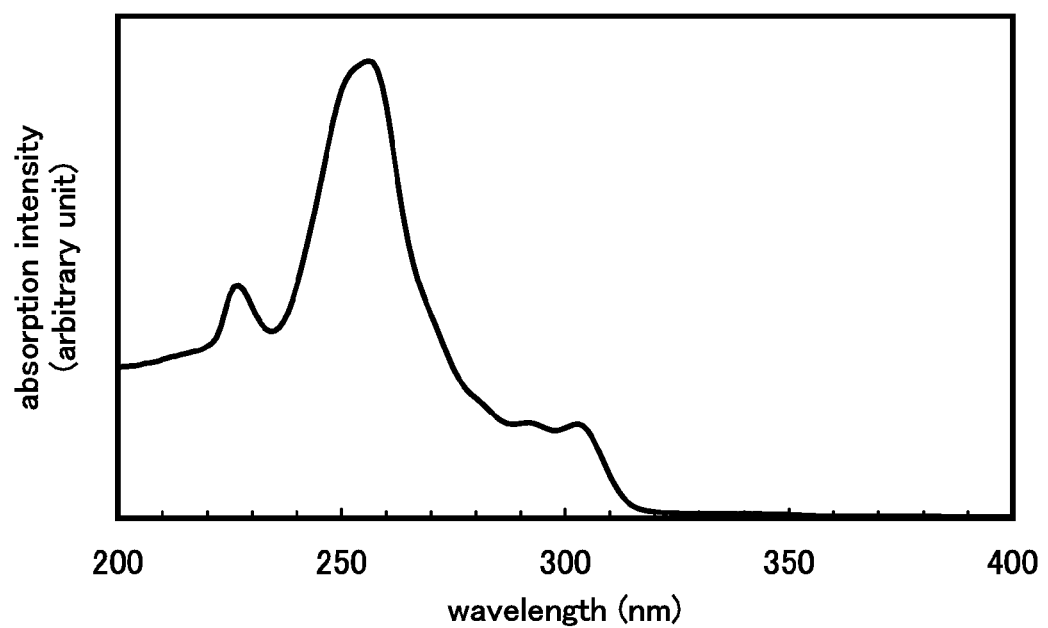
FIG. 7 shows an absorption spectrum of a dichloromethane solution of R-DOL-Pn-O1 Ph.

FIG. 7 shows an absorption spectrum of a dichloromethane solution of R-DOL-Pn-O1Ph. An ultraviolet-visible spectrophotometer (V-550, manufactured by JASCO Corporation) was used for the measurement of the absorption spectrum. The absorption spectrum in FIG. 7 was obtained by subtracting the absorption spectrum of a quartz cell filled with only dichloromethane from that of the quartz cell filled with the solution. In FIG. 7, the horizontal axis indicates wavelength (nm) and the vertical axis indicates absorption intensity (arbitrary unit). From FIG. 7, absorption was observed at around 250 nm.

The HTP of R-DOL-Pn-O1Ph synthesized in this example was approximately 60 which was measured at room temperature by the Grandjean-Cano wedge method. Thus, R-DOL-Pn-O1Ph synthesized in this example was found to have high HTP and can be favorably used as a chiral agent of a liquid crystal composition.

Example 2

In this example, liquid crystal compositions each according to one embodiment of the present invention, and liquid crystal elements including the liquid crystal compositions were made, and the characteristics of the liquid crystal compositions and the liquid crystal elements were evaluated.

Table 1 shows components of a liquid crystal composition 1 made in this example. Note that in Table 1, the mixture proportions are all represented in weight ratios; a proportion (wt %)$_{*1}$ indicates a proportion of a nematic liquid crystal and a proportion (wt %)$_{*2}$ indicates a proportion of a mixed material of a nematic liquid crystal and a chiral agent.

TABLE 1

| Material | | Proportion (wt %)$_{*1}$ | Proportion (wt %)$_{*2}$ |
|---|---|---|---|
| Nematic Liquid Crystal | E-8 | 40.1 | 92.6 |
| | CPP-3FF | 30.1 | |
| | PEP-5CNF | 29.8 | |
| Chiral Agent | R-DOL-Pn-O1Ph | | 7.4 |

In the nematic liquid crystal in the liquid crystal composition 1 made in this example, a mixed liquid crystal E8 (produced by LCC Co., Ltd.) was used as a liquid crystal 1,4-(trans-4-n-propylcyclohexyl)-3',4'-difluoro-1,1'-biphenyl (abbreviation: CPP-3FF) (produced by Daily Polymer Corporation) was used as a liquid crystal 2, and 4-n-pentylbenzoic acid 4-cyano-3-fluorophenyl ester (abbreviation: PEP-5CNF) (produced by Daily Polymer Corporation) was used as a liquid crystal 3.

Further, as the chiral agent, (4R,5R)-bis[benzyloxy-di(phenanthoren-9-yl)methyl]-2,2-dimethyl-1,3-dioxolane (abbreviation: R-DOL-Pn-O1Ph) whose synthesis method is shown in Example 1 was used. In the liquid crystal composition 1, the proportion of the chiral agent R-DOL-Pn-O1Ph in a mixed material of the nematic liquid crystal and the chiral agent is 7.4 wt %.

The following shows structural formulas of CPP-3FF (abbreviation), PEP-5CNF (abbreviation), and R-DOL-Pn-O1Ph (abbreviation) which were used in the liquid crystal composition 1 made in this example.

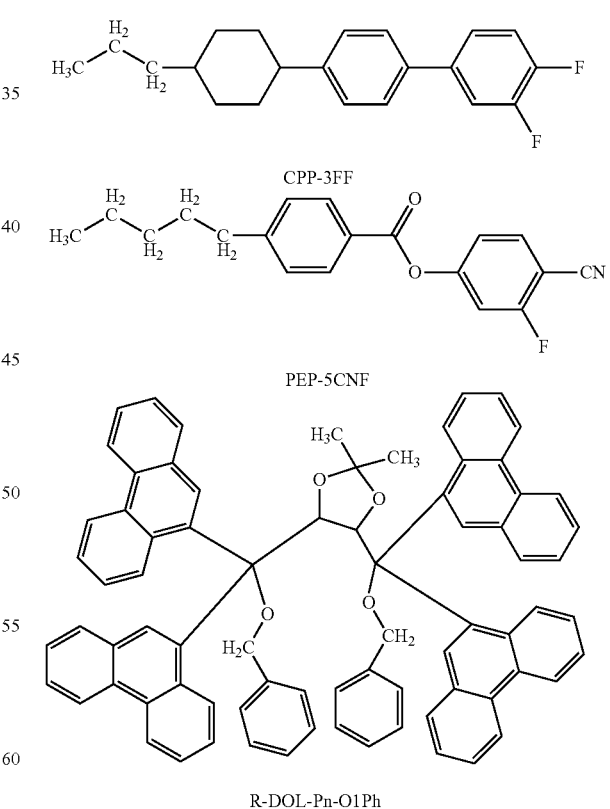

In this example, a liquid crystal element 1 was manufactured using the above liquid crystal composition 1. The following shows a manufacturing method of the liquid crystal element 1 of this example.

The liquid crystal element 1 of this example was manufactured in such a manner that a glass substrate over which a pixel electrode layer and a common electrode layer were formed and a glass substrate serving as a counter substrate were bonded to each other using sealant with a space (4 μm) provided therebetween and then a liquid crystal composition of this example, which was stirred in an isotropic phase, was injected between the substrates by an injection method.

The pixel electrode layer and the common electrode layer were formed using indium tin oxide containing silicon oxide (ITSO) by a sputtering method. The thickness of each of the pixel electrode layer and the common electrode layer was 110 nm, the width thereof was 2 μm, and the distance between the pixel electrode layer and the common electrode layer was 2 μm. Further, ultraviolet and heat curable sealing material was used as the sealant. As curing treatment, ultraviolet (irradiance of 100 mW/cm$^2$) irradiation treatment was performed for 90 seconds, and then, heat treatment was performed at 120° C. for 1 hour.

In this example, the liquid crystal composition 1 in the liquid crystal element 1 was made to exhibit an isotropic phase. Then, the liquid crystal element 1 was observed with a polarizing microscope while the temperature was decreased by 5.0° C. per minute with a temperature controller. In this manner, the temperature range where the liquid crystal composition 1 exhibited a blue phase was measured. As a result, it was confirmed that the blue phase was exhibited from 46.5° C. to 40.0° C.

The above results indicate that the liquid crystal composition according to one embodiment of the present invention can exhibit a blue phase even when the additive amount of the chiral agent is lower than or equal to 10 wt %, by including the dioxolane compound represented by the general formula (G1) as the chiral agent.

Example 3

In this example, a liquid crystal composition according to one embodiment of the present invention and a TN mode liquid crystal element including the liquid crystal composition were made, and the characteristics of the liquid crystal composition and the liquid crystal element were evaluated.

In the liquid crystal composition made in this example, a mixed liquid crystal ZLI-4792 (produced by Merck Ltd.) was used as a nematic liquid crystal and (4R,5R)-bis[benzyloxy-di(phenanthoren-9-yl)methyl]-2,2-dimethyl-1,3-dioxolane (abbreviation: R-DOL-Pn-O1Ph) whose synthesis method is shown in Example 1 was used as a chiral agent. In the liquid crystal composition, the proportion of the chiral agent R-DOL-Pn-O1Ph with respect to the nematic liquid crystal ZLI-4792 was 0.03 wt %.

The helical pitch of the liquid crystal composition made in this example was 59.5 μm, which was measured at room temperature by the Grandjean-Cano wedge method.

Then, the alignment in a transmissive TN cell before and after voltage application was observed. The TN cell used was a cell for vertical electric field application with a cell thickness of 4 μm. The pixel electrode layer was formed using indium tin oxide containing silicon oxide (ITSO) over a glass substrate by a sputtering method. The thickness was 110 nm. Then, SE-7492 (produced by Nissan Chemical Industries, Ltd.) was applied as a horizontal alignment film over each of the two glass substrates with a spin coater, and was baked at 200° C. Next, rubbing treatment was performed with a rubbing apparatus, and spacers each with a diameter of 4 μm were dispersed over one of the substrates. A heat-curable sealing material was applied over the substrate over which the spacers were dispersed, and the two substrates were bonded to each other such that the rubbing directions twist by 90°. The bonded substrates were subjected to heat treatment with a pressure of 0.3 kgf/cm$^2$ at 160° C. for 4 hours.

The substrates formed in the above manner were divided, and the liquid crystal composition was injected by an injecting method using capillary action, so that a liquid crystal element was made. This liquid crystal element was observed by transmissive crossed nicols observation with a polarizing microscope (MX-61L produced by Olympus Corporation), and line defects due to a reverse twist were not generated at all and favorable alignment was obtained.

Next, voltage-transmittance characteristics of this liquid crystal element were measured with a RETS+VT measurement system (produced by Otsuka Electronics Co., Ltd.). The voltage was applied at 0.2 V intervals in the range of 0 V to 10 V. After the measurement, transmissive crossed nicols observation with the polarizing microscope was again performed, and line defects due to the reverse twist were not generated at all and favorable alignment was obtained also after the voltage application.

The above results indicate that the liquid crystal composition according to one embodiment of the present invention can also be used for a TN mode element by including the dioxolane compound represented by the general formula (G1) and a chiral agent.

This application is based on Japanese Patent Application Serial No. 2011-260727 filed with Japan Patent Office on Nov. 29, 2011, the entire contents of which are hereby incorporated by reference.

What is claimed is:

1. A dioxolane compound represented by a general formula (G1),

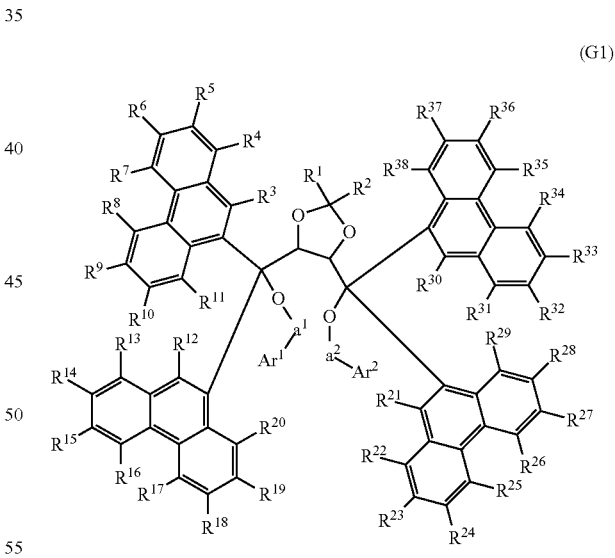

(G1)

wherein $R^1$ and $R^2$ separately represent any of hydrogen, an alkylene group having 1 to 6 carbon atoms, an alkoxy group having 1 to 20 carbon atoms, an aryl group having 6 to 12 carbon atoms, and an alkylene group having 1 to 20 carbon atoms and a phenyl group as a substituent, wherein optionally $R^1$ and $R^2$ are bonded to each other to form a ring, wherein $a^1$ and $a^2$ separately represent any of an alkylene group having 1 to 4 carbon atoms and a single bond, wherein $Ar^1$ and $Ar^2$ separately represent an aryl group having 6 to 16 carbon atoms, and wherein $R^3$ to $R^{38}$ separately represent any of hydrogen, an alkylene group having 1 to 4 carbon atoms, an alkoxy group having 1 to 4 carbon atoms, and an aryl group having 6 to 12 carbon atoms.

2. The dioxolane compound according to claim 1, wherein each of $a^1$ and $a^2$ is a is a methylene group.

3. The dioxolane compound according to claim 1, wherein $R^1$ and $R^2$ are bonded to each other to form a ring.

4. A liquid crystal composition comprising:
the dioxolane compound according to claim 1; and
a nematic liquid crystal,
wherein the liquid crystal composition exhibits a blue phase.

5. The liquid crystal composition according to claim 4, wherein a proportion of the dioxolane compound included in the liquid crystal composition is lower than or equal to 15 wt %.

6. A liquid crystal display device comprising the dioxolane compound according to claim 1.

7. The liquid crystal display device according to claim 6, wherein the liquid crystal composition comprises an organic resin.

8. A dioxolane compound represented by a general formula (G3),

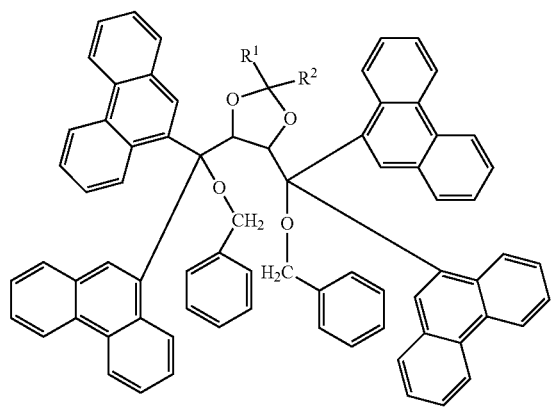

(G3)

wherein $R^1$ and $R^2$ separately represent any of hydrogen, an alkylene group having 1 to 6 carbon atoms, a methoxy group, and a phenyl group, and
wherein optionally $R^1$ and $R^2$ are bonded to each other to form a cyclohexyl ring.

9. The dioxolane compound according to claim 8, wherein $R^1$ and $R^2$ are bonded to each other to form a cyclohexyl ring.

10. A liquid crystal composition comprising:
the dioxolane compound according to claim 8; and
a nematic liquid crystal,
wherein the liquid crystal composition exhibits a blue phase.

11. The liquid crystal composition according to claim 10, wherein a proportion of the dioxolane compound included in the liquid crystal composition is lower than or equal to 15 wt %.

12. A liquid crystal display device comprising the dioxolane compound according to claim 8.

13. The liquid crystal display device according to claim 12, wherein the liquid crystal composition comprises an organic resin.

14. A dioxolane compound represented by a structural formula (101),

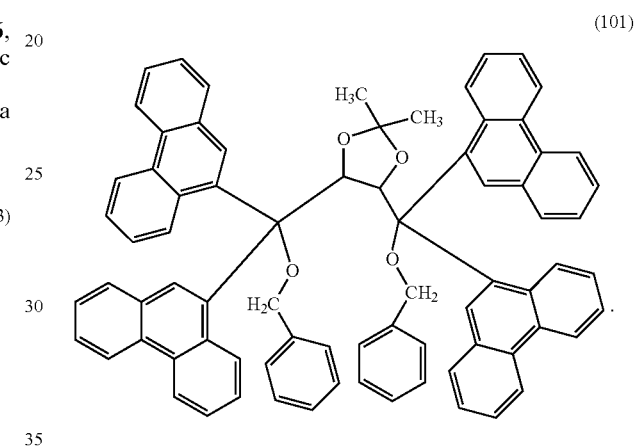

(101)

15. A liquid crystal composition comprising:
the dioxolane compound according to claim 14; and
a nematic liquid crystal,
wherein the liquid crystal composition exhibits a blue phase.

16. The liquid crystal composition according to claim 15, wherein a proportion of the dioxolane compound included in the liquid crystal composition is lower than or equal to 15 wt %.

17. A liquid crystal display device comprising the dioxolane compound according to claim 14.

18. The liquid crystal display device according to claim 17, wherein the liquid crystal composition comprises an organic resin.

* * * * *

UNITED STATES PATENT AND TRADEMARK OFFICE
CERTIFICATE OF CORRECTION

PATENT NO. : 8,668,964 B2  
APPLICATION NO. : 13/686090  
DATED : March 11, 2014  
INVENTOR(S) : Momoko Kato et al.

Page 1 of 1

It is certified that error appears in the above-identified patent and that said Letters Patent is hereby corrected as shown below:

In the Specification:

Col. 39, line 47, "approximately 60 which" should read "approximately 60 $\mu m^{-1}$, which"

In the Claims:

Col. 43, line 6, Claim 2, "is a is a methylene group." should read "is a methylene group."

Signed and Sealed this  
Twenty-second Day of July, 2014

Michelle K. Lee  
*Deputy Director of the United States Patent and Trademark Office*